(12) United States Patent
Matsuura

(10) Patent No.: US 8,594,275 B2
(45) Date of Patent: Nov. 26, 2013

(54) RADIOGRAPHIC IMAGE CAPTURING DEVICE AND COMPRESSION PADDLE

(75) Inventor: Masayoshi Matsuura, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 306 days.

(21) Appl. No.: 13/171,201

(22) Filed: Jun. 28, 2011

(65) Prior Publication Data

US 2012/0020464 A1     Jan. 26, 2012

(30) Foreign Application Priority Data

Jul. 20, 2010  (JP) ................................. 2010-163353

(51) Int. Cl.
*A61B 6/04*    (2006.01)

(52) U.S. Cl.
USPC ............................................ 378/37; 378/208

(58) Field of Classification Search
USPC ........................................... 378/37, 204, 208
See application file for complete search history.

(56) References Cited

U.S. PATENT DOCUMENTS

2008/0080668 A1*   4/2008  Kashiwagi ...................... 378/37

FOREIGN PATENT DOCUMENTS

JP          2009-285345 A      12/2009

* cited by examiner

*Primary Examiner* — Courtney Thomas
(74) *Attorney, Agent, or Firm* — McGinn IP Law Group, PLLC

(57) ABSTRACT

A radiographic image capturing device includes a subject table including a pressed surface against which a breast of a subject is pressed; and a compression paddle support portion including a first member and a second member, and to which a compression paddle is attached by sandwiching the compression paddle between the first member and the second member, and including multiple pressure sensors for detecting pressures applied to multiple sites of the attached compression paddle. At least one of the subject table or the compression paddle support portion is movable in a first direction that is toward and away from one another.

12 Claims, 19 Drawing Sheets

RADIOGRAPHIC IMAGE CAPTURING DEVICE AND COMPRESSION PADDLE

CROSS-REFERENCE TO RELATED APPLICATION

This application claims priority under 35 USC 119 from Japanese Patent Application No. 2010-163353 filed on Jul. 20, 2010, the disclosure of which is incorporated by reference herein.

BACKGROUND OF THE INVENTION

1. Field of the Invention

The present invention relates to a radiographic image capturing device that captures a radiographic image of a breast of a subject and a compression paddle that is used in a medical radiographic image capturing device.

2. Description of the Related Art

There are radiographic image capturing devices (mammography) for breasts that capture a radiographic image of a breast of a subject for the purpose of early detection of breast cancer and so forth. In this type of radiographic image capturing device, a breast that has been placed on an imaging surface of an imaging table is compressed by a compression paddle, and a radiographic image of the breast is captured in this compressed state.

In breast imaging, mirror reading—in which sets of radiographic image information of both the right and the left breasts of the same subject are acquired and compared—is performed. In this case, it is desirable for the acquired images to be bilaterally symmetrical to improve the precision of reading and diagnosis. Further, in the case of comparing a past image of the same breast of the same subject with an image to be captured this time, it is necessary for the positioning of the past image and the positioning of the image to be captured now to be the same. In order to realize such positioning, skilled advanced technology is required.

In order to grasp the positioning of the breast easily and with high precision, Japanese Patent Application Laid-Open (JP-A) No. 2009-285345, for example, discloses a mammography device that is capable of measuring the compression pressure distribution.

Meanwhile, a compression paddle may be detached from and attached to a radiographic image capturing device body. However, in the technology described in JP-A No. 2009-285345, pressure sensors are disposed integrally with the compression paddle, so pressure sensors must be provided for each compression paddle, which becomes wasteful and expensive. Further, a configuration in which pressure sensors are disposed integrally with the compression paddle is inconvenient in the case of detaching and cleaning the compression paddle.

SUMMARY

The present invention has been made in consideration of the above circumstances and provides a radiographic image capturing device with which pressure sensors can be shared between multiple compression paddles to measure pressure distribution, and a compression paddle of the same.

One aspect of the present invention is a radiographic image capturing device including: a subject table that includes a pressed surface against which a breast of a subject is pressed; and a compression paddle support portion that includes a first member and a second member, and to which a compression paddle is attached by sandwiching the compression paddle between the first member and the second member, and includes multiple pressure sensors for detecting pressures applied to multiple sites of the attached compression paddle, wherein at least one of the subject table or the compression paddle support portion is movable in a first direction that is toward and away from one another.

The above aspect may further include the compression paddle that is detachable and includes a pressing portion that presses the breast against the pressed surface.

According to the above aspect, pressure sensors can be shared between multiple compression paddles to measure pressure distribution. Further, the reproducibility of the positioning of the compression paddles that are attached and detached also improves.

In this aspect, the multiple pressure sensors may be disposed in at least one of the first halve member or the second halve member.

In this aspect, the multiple pressure sensors may be disposed on surfaces that contact the compression paddle in a state where the compression paddle has been attached.

In this aspect, the multiple pressure sensors may be disposed on surfaces where pressure drops or increases as the compression paddle presses the breast against the pressed surface.

In this aspect, one of the first halve member or the second halve member may be coupled so as to be rotatable with respect to the other.

In this aspect, one of the first halve member or the second halve member may be disposed so as to be separable with respect to the other.

According to these configurations, compression paddles that share the pressure sensors can be easily detached and attached.

In this aspect, the compression paddle support portion may be configured such that the first halve member and the second halve member are adjacent in the first direction or in a second intersecting the first.

In this aspect, the compression paddle may further include a pressing portion that presses the breast against the pressed surface, an outer peripheral wall that is disposed upright along an outer peripheral edge of the pressing portion, and multiple projecting portions that are formed on outer peripheral surfaces of the outer peripheral wall, at least one of the first member or the second member may include multiple fitting portions corresponding to the multiple projecting portions of the compression paddle, the pressure sensors may be disposed in two or more fitting portions of the multiple fitting portions, and the compression paddle may be attached by sandwiching the projecting portions between the first member and the second member in a state where the projecting portions have been fitted into the fitting portions According to these configurations, the compression paddle is stably supported and the pressure distribution can be stably measured.

In this aspect, each of the multiple pressure sensors may include a protruding portion that contacts and may be pressurized by corresponding projecting portion, the multiple pressure sensors may detect pressures applied to the protruding portions, and each of the projecting portions may include a recessed portion shallower than the protruding height of the protruding portions in a position corresponding to the protruding portion of the pressure sensor in a state where the projecting portions have been fitted into the fitting portions.

According to this configuration, pressure is stably applied to the protruding portions of the pressure sensors.

Another aspect of the present invention is a detachable compression paddle including: a pressing portion that presses a breast against the pressed surface of the radiographic image capturing device according to the above described first aspect; an outer peripheral wall that is disposed upright along an outer peripheral edge of the pressing portion; and multiple projecting portions that are formed on outer peripheral surfaces of the outer peripheral wall portion in correspondence to the fitting portions of the compression paddle support portion, wherein the compression paddle is attached to the compression paddle support portion as a result of the projecting portions being sandwiched between the first member and the second member in a state where the projecting portions have been fitted into the fitting portions of the compression paddle support portion.

Still another aspect of the present invention is a radiographic image capturing device including: a subject table that includes a pressed surface against which a breast of a subject is pressed; a detachable compression paddle that includes a pressing portion that presses the breast against the pressed surface; and a compression paddle support portion that includes a first member and a second member, and to which the compression paddle is attached by sandwiching the compression paddle between the first member and the second member, and includes multiple pressure sensors for detecting pressures applied to multiple sites of the attached compression paddle, wherein at least one of the subject table or the compression paddle support portion is movable in a first direction that is toward and away from one another.

According to these aspects, pressure sensors can be shared between multiple compression paddles to measure pressure distribution, and the reproducibility of the positioning of the compression paddles that are attached and detached also improves.

BRIEF DESCRIPTION OF THE DRAWINGS

An exemplary embodiment of the present invention will be described in detail based on the following figures, wherein.

DETAILED DESCRIPTION

Figure 1:
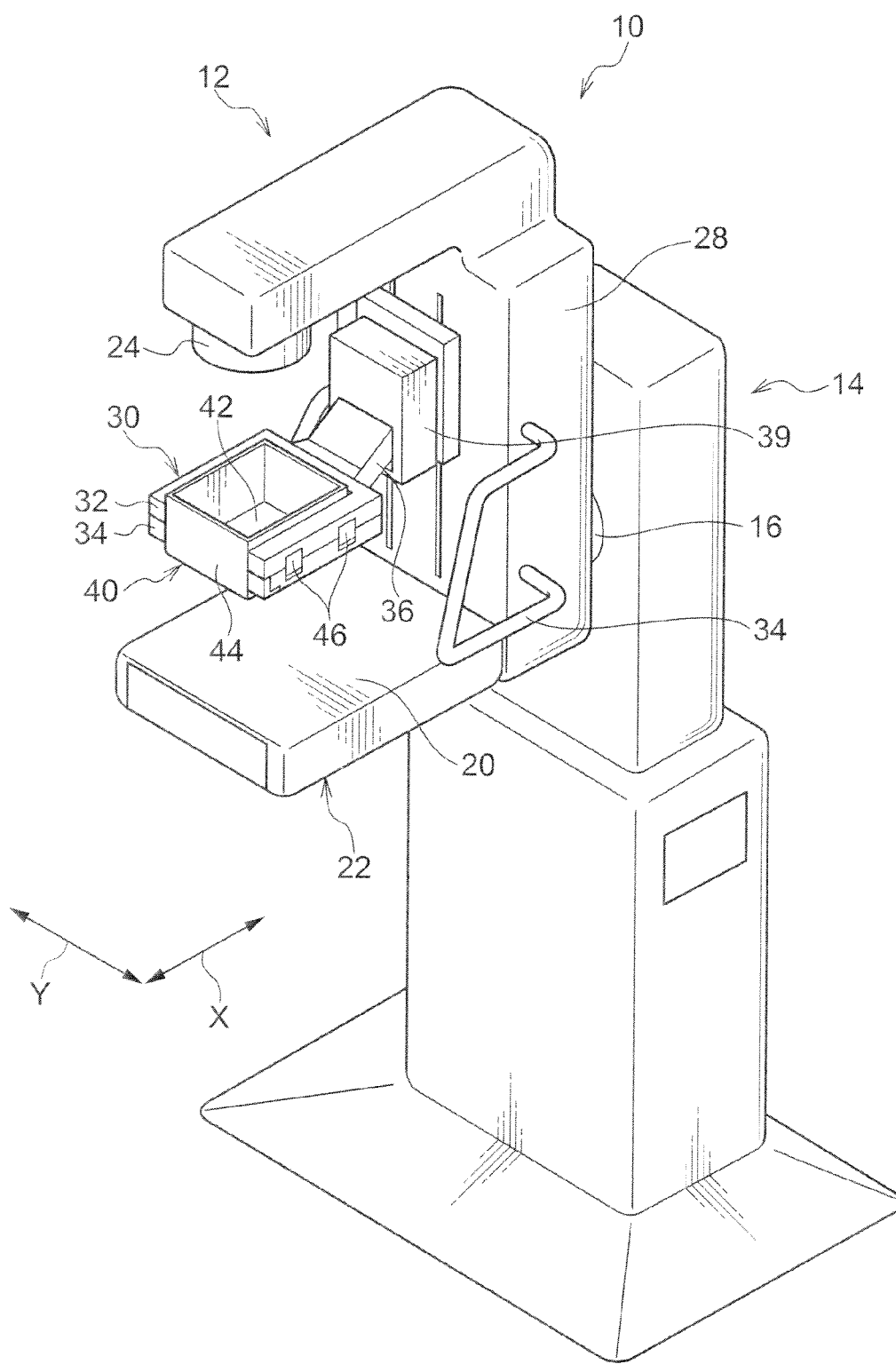
FIG. 1 is a perspective view of an X-ray imaging device that is an exemplary embodiment of a radiographic image capturing device.

FIG. 1 is a perspective view of an X-ray imaging device (a mammography device) 10 that is an exemplary embodiment of the radiographic image capturing device. The X-ray imaging device 10 captures an X-ray image of a breast of a subject and can perform both craniocaudal (CC) imaging and mediolateral oblique (MLO) imaging. The direction of arrow X in FIG. 1 represents the front-rear direction of the X-ray imaging device 10 (device front side-device back side direction), and the direction of arrow Y in FIG. 1 represents the left-right direction of the X-ray imaging device 10 (device left side-device right side direction).

The X-ray imaging device 10 is equipped with a measuring portion 12, which is disposed on the device front side and has a substantially square C shape as seen in a side view, and a stand portion 14, which supports the measuring portion 12 from behind. A rotating shaft 16 that extends out from the device back side and is rotatably supported in the stand portion 14 is disposed in the measuring portion 12. The measuring portion 12 is rotatably supported on the stand portion 14 as a result of the rotating shaft 16 being supported in the stand portion 14.

The measuring portion 12 is equipped with an imaging table 22, a radiation irradiation device 24, and a holding portion 28. The imaging table 22 has an imaging surface 20 serving as a flat pressed surface against which the breast of the subject is pressed and has a radiation detector (not shown) that detects radiation to acquire a radiographic image. The radiation irradiation device 24 serves as an X-ray source in which an X-ray tube (not shown) is disposed and emits X-rays for inspection toward the imaging surface 20. The holding portion 28 holds the imaging table 22 and the radiation irradiation device 24. The imaging table 22 of the present embodiment corresponds to a subject table of the present invention and is configured to double as a subject table on which a breast that is an imaging subject is placed and as an imaging table for imaging.

The holding portion 28 holds the imaging table 22 and the radiation irradiation device 24 such that the imaging surface 20 and the radiation irradiation device 24 are a predetermined distance apart from each other. Further, a compression paddle support portion 30 is disposed on the holding portion 28. The compression paddle support portion 30 has a divided structure including a first divisional member 32 and a second divisional member 34. Moreover, the compression paddle support portion 30 is equipped with a coupling portion 36, a hinge portion 38, and a sliding support portion 39.

The sliding support portion 39 is disposed so as to be slidable between the imaging surface 20 and the radiation irradiation device 24. The sliding support portion 39 is coupled to the second divisional member 34 via the coupling portion 36. The first divisional member 32 and the second divisional member 34 are coupled together via the hinge portion 38, and the first divisional member 32 is configured to be rotatable with respect to the second divisional member 34.

A compression paddle 40 detachable from the compression paddle support portion 30, which will be described in detail later, is attached to and supported by the compression paddle support portion 30 in a state where the compression paddle 40 has been sandwiched between the first divisional member 32 and the second divisional member 34. Because of this configuration, the compression paddle 40 can move in a direction toward and away from the imaging surface 20 (i.e., an opposing direction to the imaging surface 20) integrally with the sliding support portion 39 in a state where the compression paddle 40 has been attached to the compression paddle support portion 30.

A pair of handles 34 that a subject can grip with both hands at the time of imaging are disposed on the holding portion 28 so as to sandwich the imaging surface 20. Further, an X-ray detector (not shown) serving as the radiation detector that is irradiated with the radiation that has passed through the imaging surface 20 is disposed inside the imaging table 22.

Figure 2:
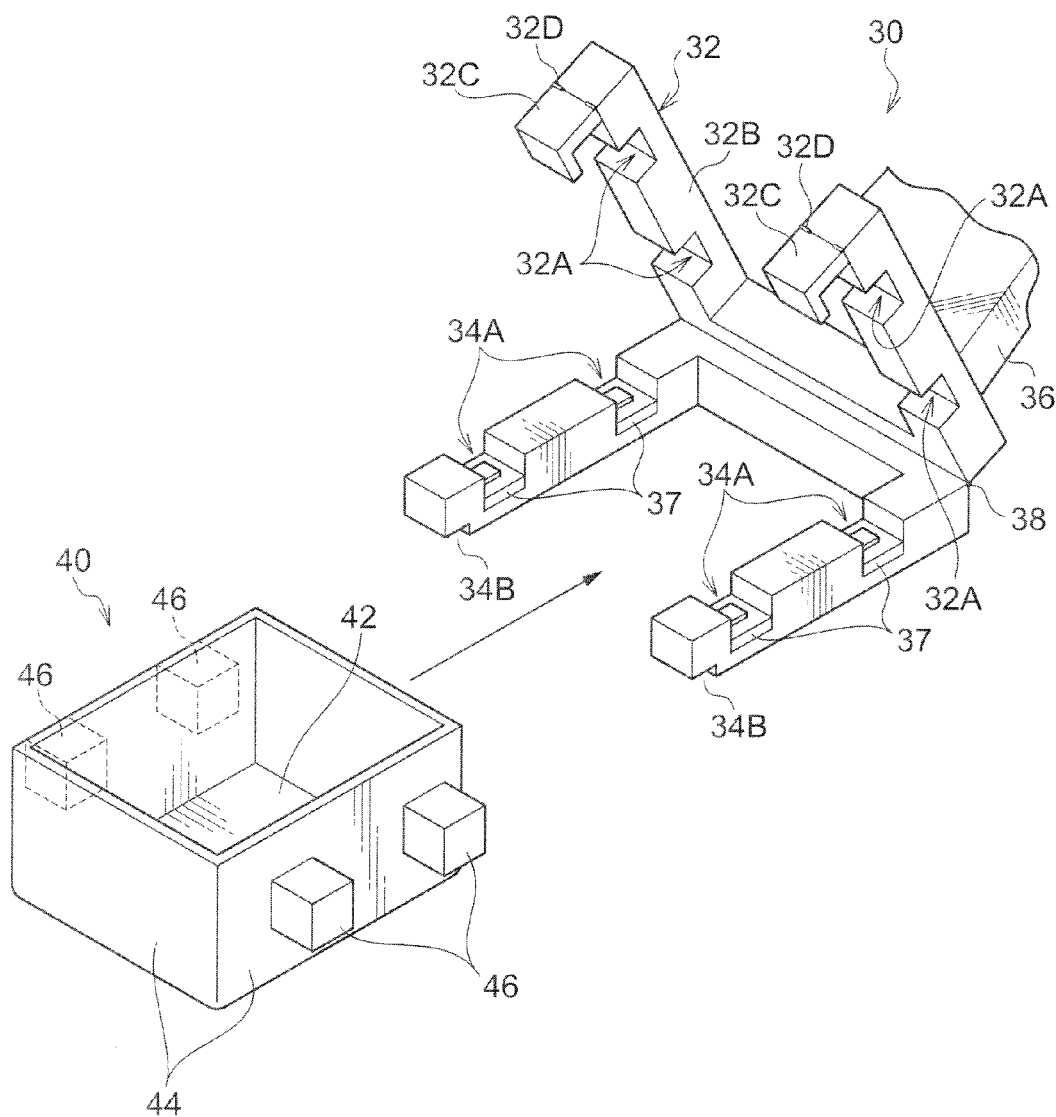
FIG. 2 shows a perspective view of a compression paddle that has been detached from a compression paddle support portion and a perspective view of the compression paddle support portion when the compression paddle has been detached therefrom and the compression paddle support portion is in an open state.
Figure 3A:
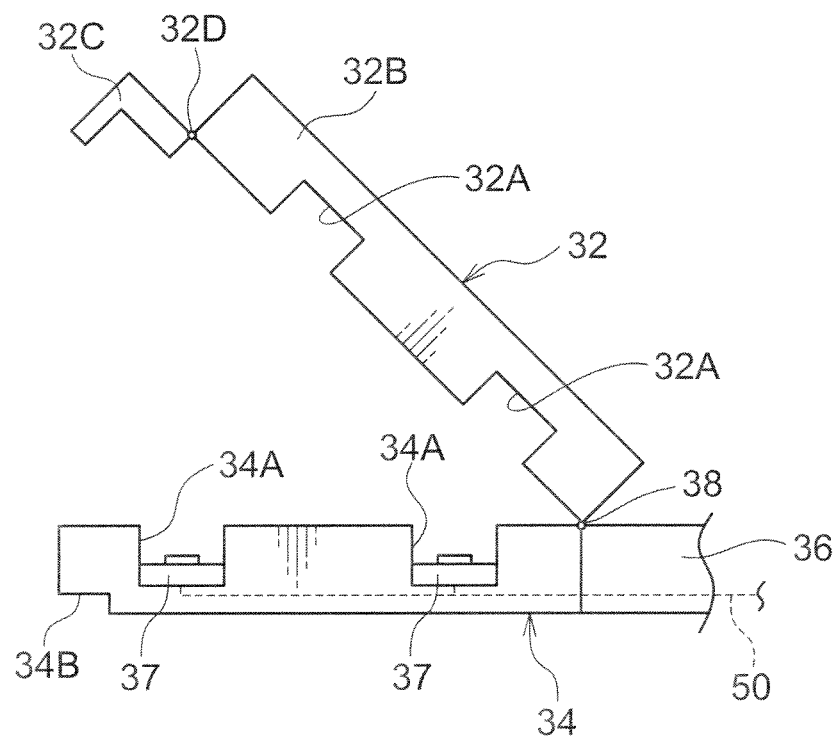
FIG. 3A is a side view of the compression paddle support portion when it is in the open state.
Figure 3B:
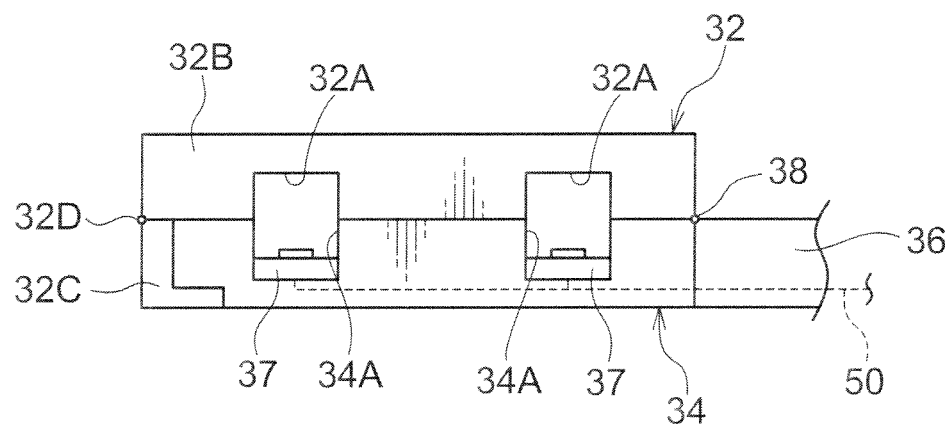
FIG. 3B is a side view of the compression paddle support portion when it is in a closed state.

The detailed configurations of the compression paddle support portion 30 and the compression paddle 40 will be described with reference to FIG. 2, FIG. 3A, and FIG. 3B. FIG. 2 shows a perspective view of the compression paddle 40 that has been detached from the compression paddle support portion 30 and a perspective view of the compression paddle support portion 30 when the compression paddle 40 has been detached therefrom and the compression paddle support portion 30 is in an open state. FIG. 3A is a side view of the compression paddle support portion 30 when it is in a state where the lower surface of the first divisional member 32 and the upper surface of the second divisional member 34 are apart from each other (the open state). FIG. 3B is a side view of the compression paddle support portion 30 when it is in a state where the lower surface of the first divisional member 32 and the upper surface of the second divisional member 34 are contacting each other (a closed state).

The compression paddle 40 has a pressing portion 42 that presses the breast of the subject against the imaging surface 20, an outer peripheral wall 44 that is disposed upright along the outer peripheral edge of the pressing portion 42, and multiple projecting portions 46 that are formed on outer peripheral surfaces of the outer peripheral wall 44. In the present embodiment, the projecting portions 46 are formed two each on an opposing pair of outer peripheral surfaces of the outer peripheral wall 44. Further, in the present embodiment, the pressing portion 42 and the outer peripheral wall 44 are integrally formed.

The second divisional member 34 of the compression paddle support portion 30 is formed in a substantially square C shape as seen in a plan view and is coupled in a fixed state to the sliding support portion 39 via the coupling portion 36. Recessed portions 34A serving as fitting portions into which the projecting portions 46 are fitted are formed in the second divisional member 34 in positions corresponding to the projecting portions 46 disposed on the compression paddle 40. Further, cutout portions 34B are formed in the two distal end portions of the second divisional member 34.

Figure 4:
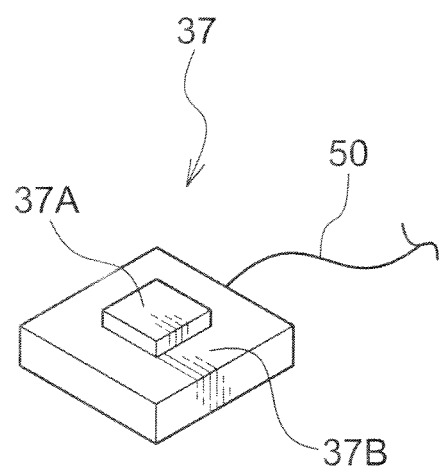
FIG. 4 is a perspective view of a pressure sensor.

Pressure sensors 37 are disposed on the bottom surfaces of the recessed portions 34A of the second divisional member 34. As shown in FIG. 4, each of the pressure sensors 37 has a protruding portion 37A and a substrate 37B. The protruding portions 37A contact and are pressurized by the projecting portions 46 of the compression paddle 40. The substrates 37B are disposed with signal processors that convert a physical quantity (electrical resistance, electrostatic capacitance, etc.) that changes due to the pressure with which the protruding portions 37A have been pressurized into electrical signals. The pressure sensors 37 are configured to detect the pressures applied to the protruding portions 37A. The pressure sensors 37 are not particularly limited, and may be semiconductor pressure sensors, whose electrical resistance changes in response to the bending of a silicon chip when pressure is applied to the silicon chip and by which the change in the electrical resistance is converted into an electrical signal so that the pressure is detected, or electrostatic capacitance pressure sensors, which convert the displacement of electrostatic capacitance when a movable electrode is moved by pressure into an electrical signal and detects the pressure. The protruding portions 37A receive the pressures and are communicated with the silicon chips or the movable electrodes whose physical quantity changes. The electrical signals representing the detected pressures are transmitted to a later-described compression mechanism 70 by a signal line 50.

The first divisional member 32 is formed in a substantially square C shape as seen in a plan view, is coupled to the second divisional member 34 via the hinge portion 38, and is configured to be rotatable in the moving direction of the sliding support portion 39. Recessed portions 32A serving as fitting portions into which the projecting portions 46 are fitted are formed in a body 32B of the first divisional member 32. Engaging portions 32C are coupled to the body 32B of the first divisional member 32 via hinge portions 32D, and the engaging portions 32C are configured to be rotatable with respect to the body 32B. As shown in FIG. 3B, the engaging portions 32C are formed such that they engage with the cutout portions 34B of the second divisional member 34 in the closed state of the compression paddle support portion 30. It is preferable for the recessed portions 32A and the recessed portions 34A to be formed in a shape and a size with which the compression paddle 40 is stably supported when the projecting portions 46 of the compression paddle 40 have been fitted into them.

Figure 5:
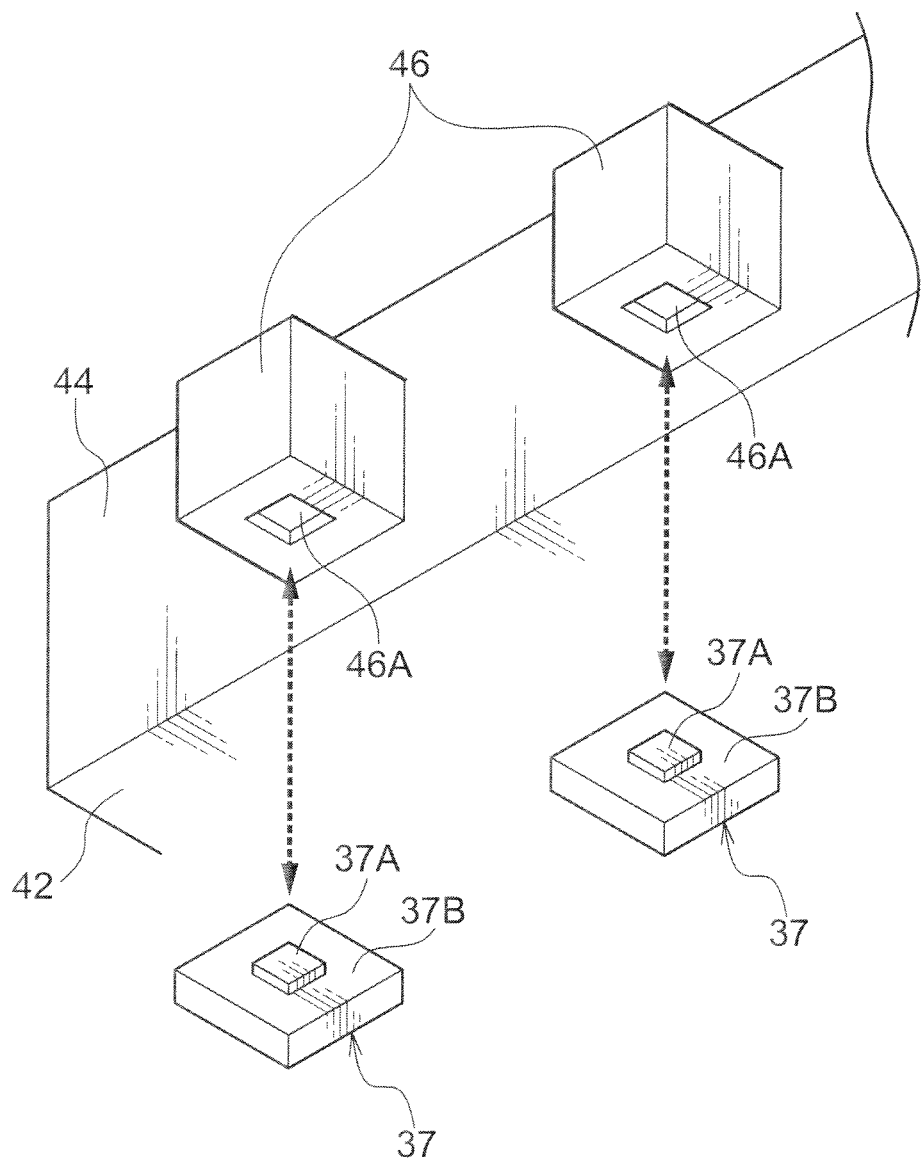
FIG. 5 is a diagram showing projecting portions of the compression paddle in which recessed portions are formed.

As shown in FIG. 5, in the projecting portions 46 of the compression paddle 40, recessed portions 46A shallower than the protruding height of the protruding portions 37A are disposed in positions in the projecting portions 46 corresponding to the protruding portions 37A of the pressure sensors 37 in a state where the projecting portions 46 of the compression paddle 40 have been fitted into the recessed portions 34A. Because of this, positional shifting when the projecting portions 46 have been fitted into the recessed portions 34A is suppressed, and pressure is stably applied to the protruding portions 37A of the pressure sensors 37.

Figure 6:
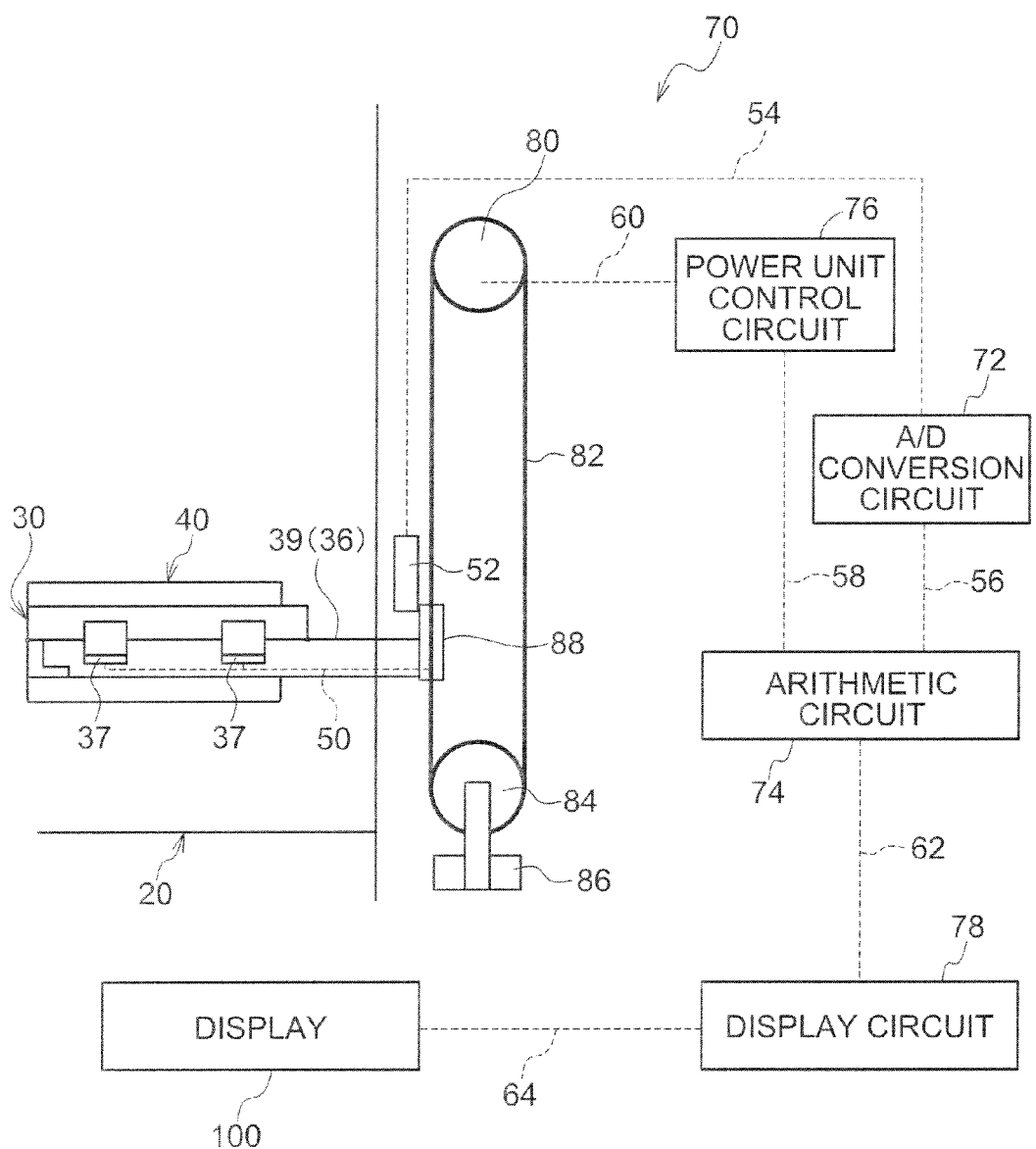
FIG. 6 is a configuration diagram schematically showing the configuration of a compression mechanism disposed in the radiographic image capturing device.

Next, a compression mechanism 70 disposed in the radiographic image capturing device 10 will be described using FIG. 6. The compression mechanism 70 displays on an external display 100 the pressure distribution detected by the pressure sensors 37 and controls the moving amount and the moving direction of the sliding support portion 39.

The compression mechanism 70 is equipped with a power unit 80, a belt 82, a pulley 84, a pulley fixing member 86, and a support portion fixing member 88. The power unit 80 applies a rotational force to the belt 82. The belt 82 is wound around the pulley 84, which is fixed by the pulley fixing member 86, and is rotated by the rotational force applied by the power unit 80. The support portion fixing member 88 is disposed on the belt 82. The sliding support portion 39 is fixedly connected to the support portion fixing member 88, and the sliding support portion 39 moves when the belt 82 rotates.

Moreover, the compression mechanism 70 is equipped with an amplifier board 52, an A/D conversion circuit 72, an arithmetic circuit 74, a power unit control circuit 76, and a display circuit 78.

The amplifier board 52 amplifies the analog electrical signals that have been inputted via the signal line 50 from the multiple pressure sensors 37. The A/D conversion circuit 72 converts the analog electrical signals that have been inputted via a signal line 54 from the amplifier board 52 into digital electrical signals. The arithmetic circuit 74 determines the two-dimensional distribution of the compression pressure along the pressing surface of the pressing portion 42 of the compression paddle 40 by performing interpolation processing on the basis of the digital electrical signals that have been inputted via a signal line 56 from the A/D conversion circuit 72. Moreover, the arithmetic circuit 74 generates control signals for controlling the moving amount and the moving direction of the sliding support portion 39 on the basis of the digital electrical signals that have been inputted (or the two-dimensional distribution of the compression pressure that has determined by arithmetic calculation) and outputs the control signals to the power unit control circuit 76 via a signal line 58. The arithmetic circuit 74 also generates display signals for causing the two-dimensional distribution to be displayed on the external display 100 on the basis of the two-dimensional distribution of the compression pressure that has determined and outputs the display signals to the display circuit 78 via a signal line 62.

The power unit control circuit 76 drives the power unit 80 via a signal line 60 on the basis of the control signals that have been inputted from the arithmetic circuit 74 and controls the moving amount and the moving direction of the sliding support portion 39. The display circuit 78 controls the external display 100 via a signal line 64 on the basis of the display signals that have been inputted from the arithmetic circuit 74 and causes the pressure distribution to be displayed.

In the components of the compression mechanism 70, components other than the power unit 80, the belt 82, the pulley 84, the pulley fixing member 86, and the support portion fixing member 88 may be disposed in a device outside the X-ray imaging device 10.

Figure 7:
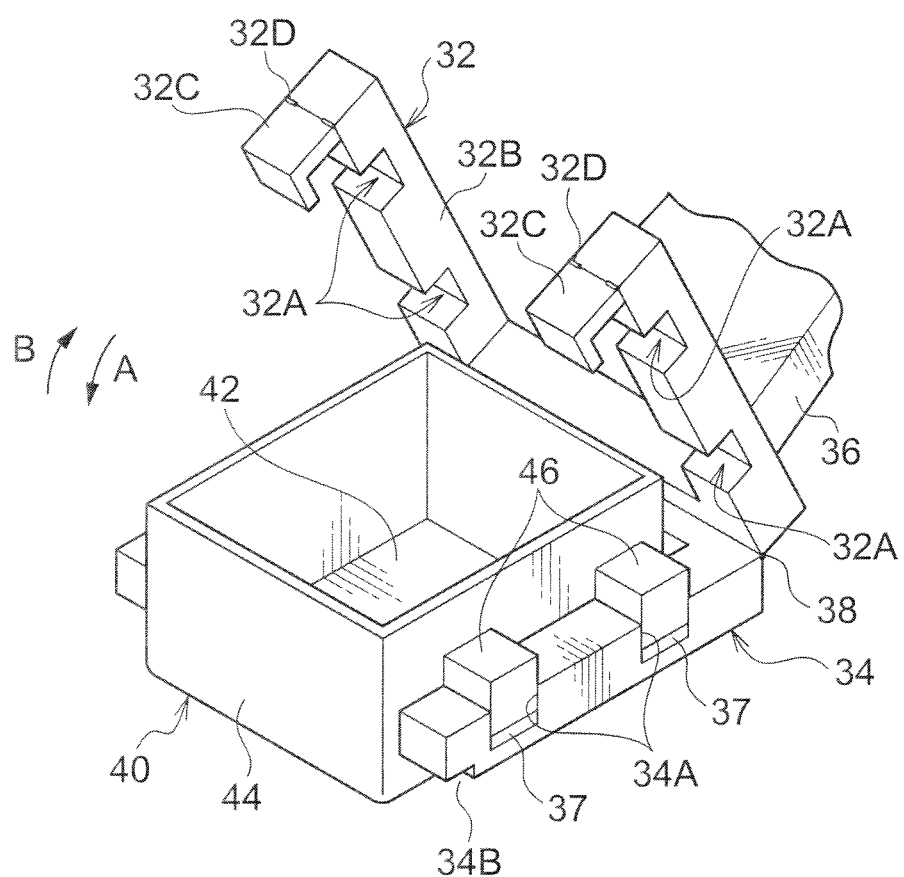
FIG. 7 is a perspective view showing a state where the projecting portions of the compression paddle have been fitted into recessed portions of a second divisional member of the compression paddle support portion in the open state.

The procedure of attaching the compression paddle 40 to the compression paddle support portion 30 will be described with reference to FIG. 2, FIG. 7, and FIG. 8.

As shown in FIG. 2, the first divisional member 32 is rotated in the direction away from the second divisional member 34 to place the compression paddle support portion 30 in the open state. Then, the projecting portions 46 of the compression paddle 40 are brought into alignment with the positions of the recessed portions 34A of the second divisional member 34 and are fitted into the recessed portions 34A of the second divisional member 34 from above the second divisional member 34. At this time, the protruding portions 37A of the pressure sensors 37 are fitted into the recessed portions 46A of the projecting portions 46. As a result, as shown in FIG. 7, the lower-side portions of the projecting portions 46 of the compression paddle 40 become fitted into the recessed portions 34A. From this state, the first divisional member 32 is rotated in the direction toward the second divisional member 34 (the direction of arrow A) to place the compression paddle support portion 30 in the closed state. Thus, the upper-side portions of the projecting portions 46 of the compression paddle 40 are fitted into the recessed portions 32A of the first divisional member 32. At this time, the engaging portions 32C of the first divisional member 32 are caused to engage with the cutout portions 34B of the second divisional member 34. FIG. 8 shows a state where the compression paddle 40 has been attached to the compression paddle support portion 30.

In this way, as shown in FIG. 1, the compression paddle 40 is attached to the compression paddle support portion 30 in a state where the compression paddle 40 is sandwiched between the first divisional member 32 and the second divisional member 34 in an orientation where the pressing surface of the pressing portion 42 of the compression paddle 40 opposes the imaging surface 20.

In a case where CC imaging is performed using the X-ray imaging device 10 in a state where the compression paddle 40 has been attached in this way, first, the breast of the subject is placed on the imaging surface 20 of the imaging table 22. After the breast has been placed in a predetermined position, the sliding support portion 39 is slid toward the imaging table 22 to move the compression paddle 40 closer toward the imaging surface 20. Then, the breast is pressed against the imaging surface 20 by the approaching compression paddle 40 and is spread out to a thickness with which a clear radiographic image is obtained even in a state where the radiation output has been lowered to suppress exposure of the examinee to radiation. Because the engaging portions 32C of the first divisional member 32 are engaged with the cutout portions 34B of the second divisional member 34 as mentioned above, the breast can be pressed without the compression paddle 40 coming out of the compression paddle support portion 30. Thereafter, in a state where the breast is compressed, radiation is irradiated from the radiation irradiation device 24, the radiation dose that has passed through the breast is detected by the radiation detector (not shown) of the imaging table 22, and a radiographic image is formed.

Figure 9A:
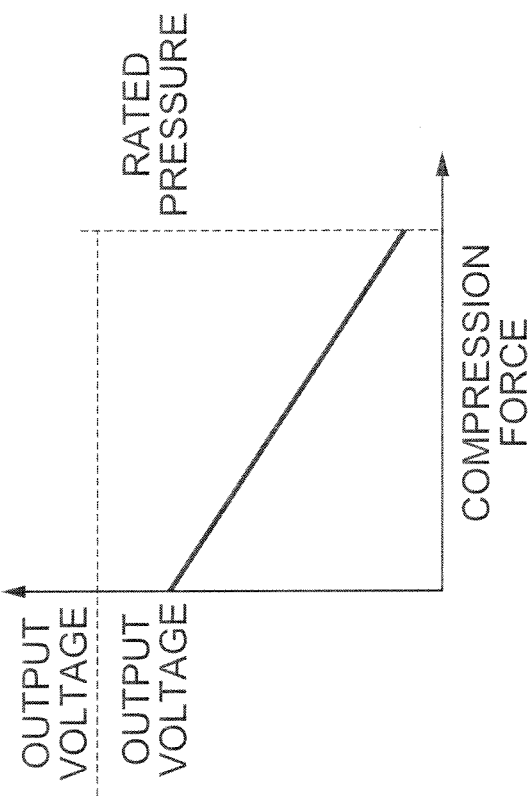
FIG. 9A and FIG. 9B are explanatory diagrams describing a characteristic of the pressure sensors and a change in pressure applied to the pressure sensors at a time when the pressure sensors are in use.

Here, the characteristic of the pressure sensors 37 and the change in the pressures applied to the pressure sensors 37 at the time when the pressure sensors 37 are in use will be described. As shown in FIG. 9A, the electrical signal (output voltage) outputted by each of the pressure sensors 37 becomes larger the larger the applied pressure is. In the present embodiment, when the compression paddle 40 is moved closer toward the imaging surface 20 and the breast is pressed against the imaging surface 20, stress from the imaging table 22 acts on the compression paddle 40, and a force works in a direction in which the compression paddle 40 moves upward (toward the radiation irradiation device 24). Consequently, for example, in a case where the pressure sensors 37 have been disposed on the first divisional member 32 side, as shown in FIG. 9A, the pressure acting on each of the pressure sensors 37 may be larger the larger the force that presses the breast (hereinafter "compression force") is, so depending on the compression force, a case where the compression force exceeds the rated pressure of the pressure sensors 37 may arise.

Figure 9B:
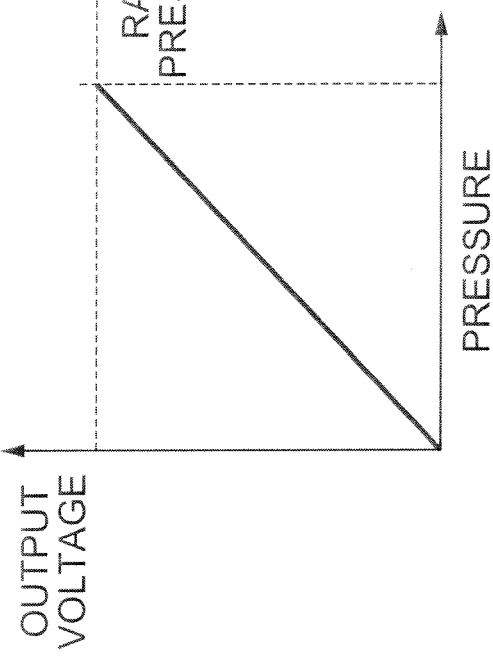

However, in the present embodiment, the pressure sensors 37 are disposed on the bottom surfaces of the recessed portions 34A of the second divisional member 34. For that reason, as shown in FIG. 9B, the pressure acting on each of the pressure sensors 37 becomes the largest in a state where the compression paddle 40 is attached to the compression paddle support portion 30 and does not contact the breast. When the compression paddle 40 contacts the breast and pressing of the breast is started, the pressure applied to each of the pressure sensors 37 becomes smaller the larger the compression force becomes (that is, as the compression paddle 40 presses the breast against the imaging surface 20). Consequently, the pressure applied to each of the pressure sensors 37 at the time when the compression paddle 40 is in use does not exceed the rated pressure.

Further, in the present embodiment, whether or not the compression paddle 40 is appropriately attached can also be checked by the output voltages at the time when the compression paddle 40 is attached.

Figure 8:
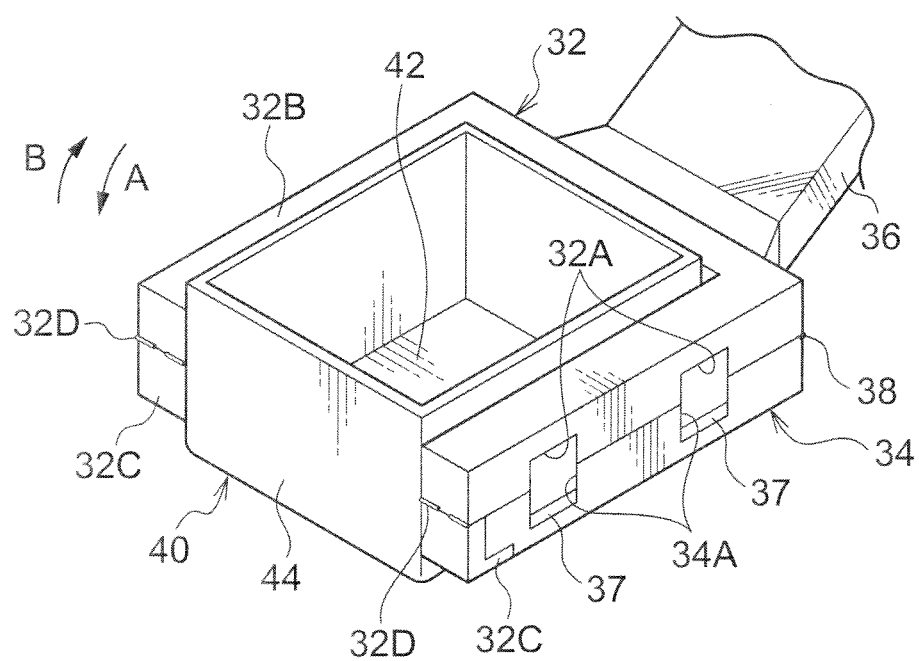
FIG. 8 is a perspective view showing the compression paddle support portion and the compression paddle when the compression paddle has been attached to the compression paddle support portion and the compression paddle support portion has been placed in the closed state.

In a case where the compression paddle 40 is detached from the compression paddle support portion 30, the engaging portions 32C of the first divisional member 32 are rotated in the direction of arrow B from the state shown in FIG. 8 to disengage them from the cutout portions 34B of the second divisional member 34. Moreover, in this state, the entire first divisional member 32 is rotated in the direction away from the second divisional member 34 and the projecting portions 46 of the compression paddle 40 are removed from the recessed portions 32A of the first divisional member 32 to place the compression paddle support portion 30 in the open state as shown in FIG. 7. In this state, the compression paddle 40 is lifted up, the projecting portions of the compression paddle 40 are removed from the recessed portions 34A of the second divisional member 34, and the compression paddle 40 is detached from the compression paddle support portion 30 as shown in FIG. 2.

It is preferable for the corner portions of the projecting portions 46 and the recessed portions 32A to be formed in a chamfered state so that the projecting portions 46 of the compression paddle 40 easily fit into the recessed portions 32A of the first divisional member 32, but illustration thereof is omitted in the drawings used in the above description.

As described above, the compression paddle support portion 30 has a divided structure, the compression paddle 40 is attached by sandwiching the compression paddle 40 in the compression paddle support portion 30, and the multiple pressure sensors 37 for detecting pressures applied to multiple sites of the attached compression paddle 40 are disposed in the compression paddle support portion 30. For this reason, even in a case where multiple types of the compression paddle 40 are used in capturing a radiographic image, the pressure sensors 37 can be shared by the multiple types of the compression paddles 40 to measure the pressure distribution. Because the compression paddle 40 can be easily attached and detached due to the divided structure, this is convenient when, for example, replacing the compression paddle 40 or detaching the compression paddle 40 for cleaning. Moreover, the reproducibility of the positioning of the compression paddle 40 that is detachable improves due to the obtained pressure distribution. The projecting portions 46 of each compression paddle 40 supported in the compression paddle support portion 30 are formed so as to be capable of fitting into the recessed portions of the compression paddle support portion 30.

In the above exemplary embodiment, all of the multiple projecting portions 46 of the compression paddle 40 are given the same shape (a substantially rectangular shape as seen in a side view), but embodiments are not limited to this. For example, at least one of the multiple projecting portions 46 may be formed in a shape differing from that of the other projecting portions 46.

Figure 10A:
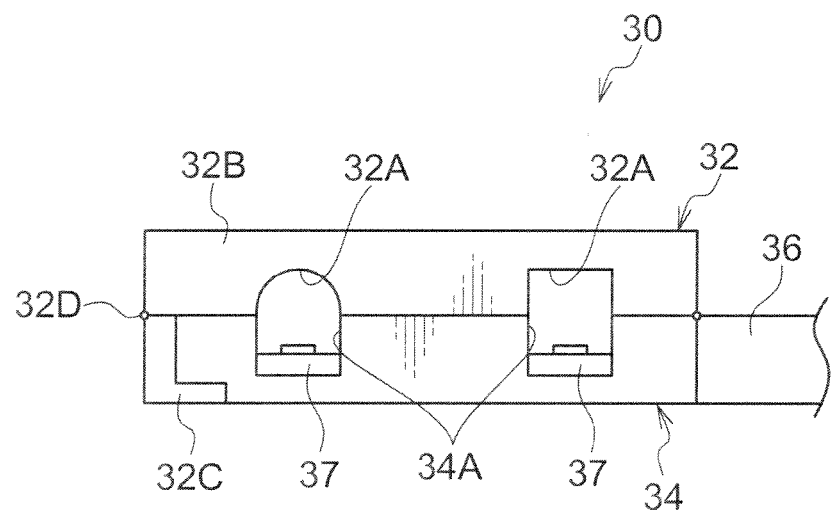
FIG. 10A is a side view of the compression paddle support portion that supports the compression paddle of FIG. 10B.
Figure 10B:
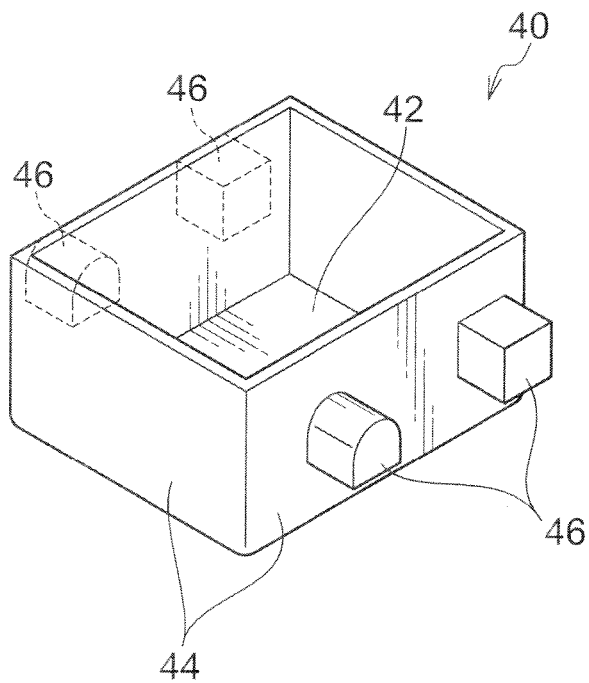
FIG. 10B is a perspective view of the compression paddle in a case where at least one of the projecting portions of the compression paddle is formed in a substantial artillery shell shape as seen in a side view (or a cross-sectional view)
Figure 11A:
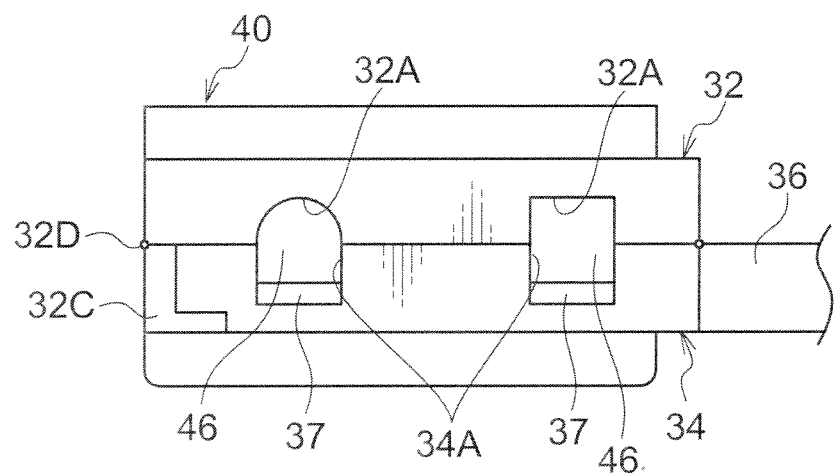
FIG. 11A is a side view when the compression paddle shown in FIG. 10B has been attached to the compression paddle support portion shown in FIG. 10A.
Figure 11B:
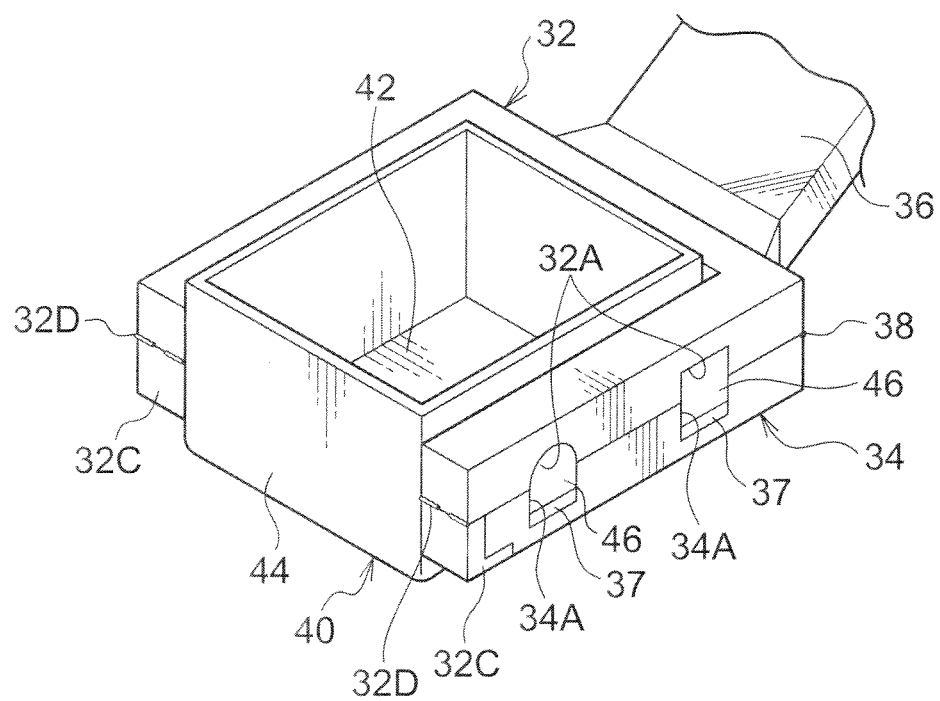
FIG. 11B is a diagram showing a perspective view when the compression paddle shown in FIG. 10B has been attached to the compression paddle support portion shown in FIG. 10A.

For example, as shown in FIG. 10B, the shapes of the two projecting portions 46 of the four projecting portions 46 of the compression paddle 40 that are fitted into the recessed portions 32A on the distal end portion side of the first divisional member 32 and the recessed portions 34A on the distal end portion side of the second divisional member 34 may be formed in a substantial artillery shell shape when seen in a side view (or a cross-sectional view). In this case, as shown in FIG. 10A, the recessed portions 32A on the distal end side of the first divisional member 32 and the recessed portions 34A on the distal end side of the second divisional member 34 are formed such that the shapes of the fitting portions formed by the recessed portions 32A on the distal end side of the first divisional member 32 and the recessed portions 34A on the distal end side of the second divisional member 34 have a substantial artillery shell shape when seen in a side view (or a cross-sectional view) when the compression paddle support portion 30 is in the closed state. FIG. 11A shows a side view when the compression paddle 40 shown in FIG. 10B has been attached to the compression paddle support portion 30 shown in FIG. 10A, and FIG. 11B shows a perspective view when the compression paddle 40 shown in FIG. 10B has been attached to the compression paddle support portion 30 shown in FIG. 10A.

Figure 12A:
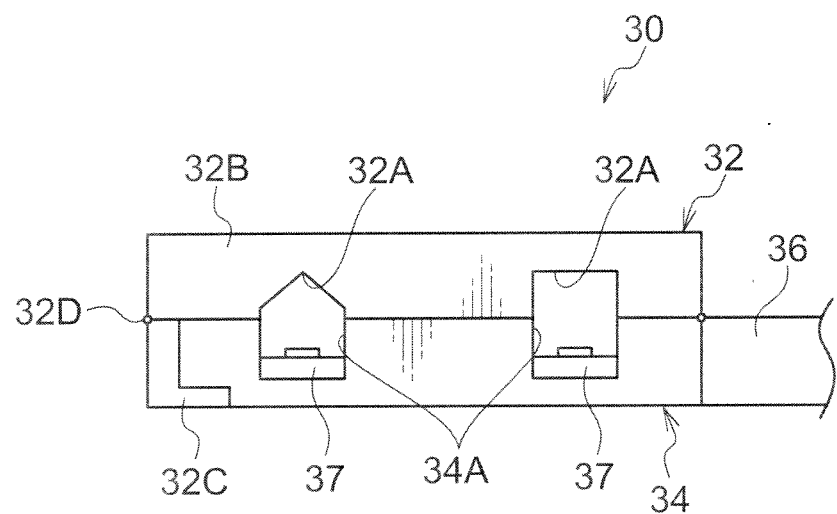
FIG. 12A is a side view of the compression paddle support portion that supports the compression paddle of FIG. 12B.
Figure 12B:
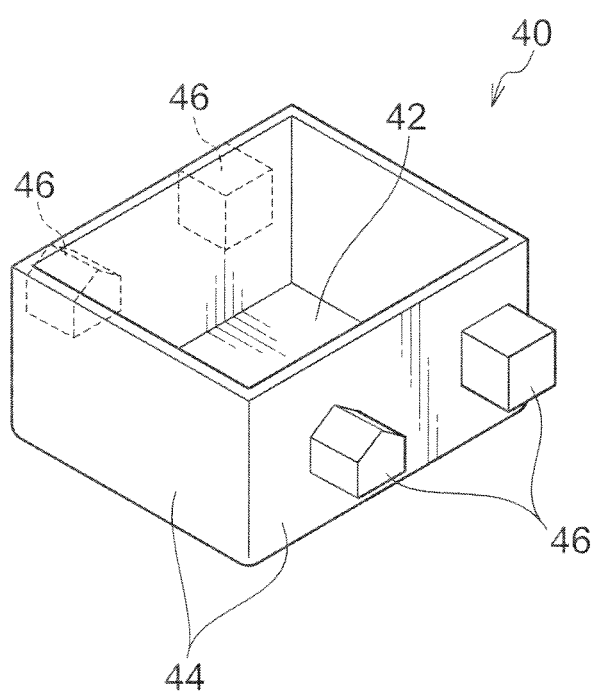
FIG. 12B is a perspective view of the compression paddle in a case where at least one of the projecting portions of the compression paddle is formed in a substantial home plate shape as seen in a side view (or a cross-sectional view)
Figure 13A:
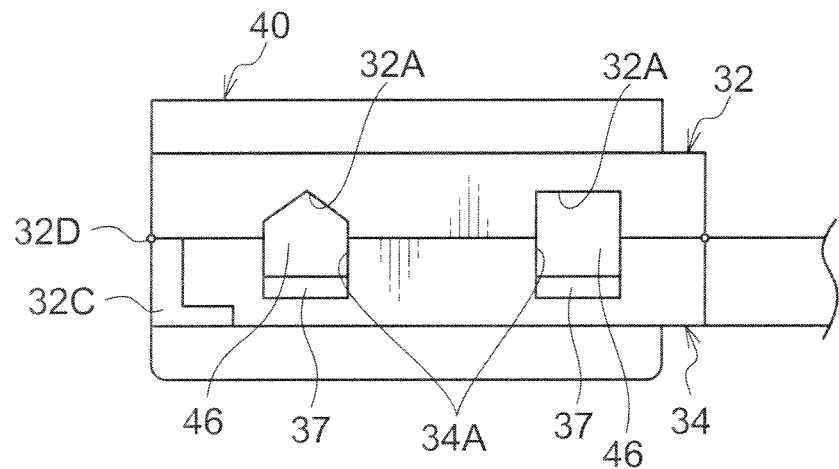
FIG. 13A is a side view when the compression paddle shown in FIG. 12B has been attached to the compression paddle support portion shown in FIG. 12A.
Figure 13B:
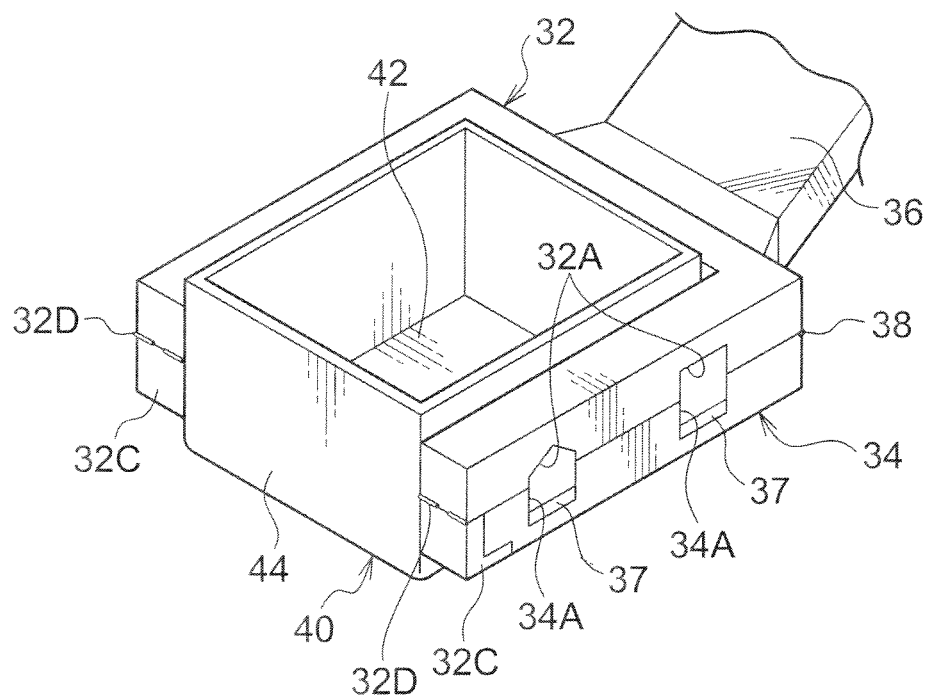
FIG. 13B is a diagram showing a perspective view when the compression paddle shown in FIG. 12B has been attached to the compression paddle support portion shown in FIG. 12A.

Further, as shown in FIG. 12B, the shapes of the two projecting portions 46 of the four projecting portions 46 of the compression paddle 40 that are fitted into the recessed portions 32A on the distal end side of the first divisional member 32 and the recessed portions 34A on the distal end side of the second divisional member 34 may be formed in a substantial home plate shape when seen in a side view. In this case, as shown in FIG. 12A, the recessed portions 32A on the distal end side of the first divisional member 32 and the recessed portions 34A on the distal end side of the second divisional member 34 are formed such that the shapes of the fitting portions formed by the recessed portions 32A on the distal end side of the first divisional member 32 and the recessed portions 34A on the distal end side of the second divisional member 34 have a substantial home plate shape when seen in a side view when the compression paddle support portion 30 is in the closed state. FIG. 13A shows a side view when the compression paddle 40 shown in FIG. 12B has been attached to the compression paddle support portion 30 shown in FIG. 12A, and FIG. 13B shows a perspective view when the compression paddle 40 shown in FIG. 12B has been attached to the compression paddle support portion 30 shown in FIG. 12A.

In this way, by forming at least one of the multiple projecting portions 46 in a shape differing from that of the other projecting portions 46, the compression paddle 40 can be prevented from being attached in a front-back reversed orientation with respect to the compression paddle support portion 30 when attaching the compression paddle 40.

Here, examples where the shape of at least one of the projecting portions 46 is made different have been described, but embodiments are not limited thereto and the size of at least one of the projecting portions 46 may be made different. Further, both the shape and the size may be made different. In any case, the recessed portions 32A and the recessed portions 34A corresponding to the projecting portions 46 are formed in a shape and a size according to the shape and the size of the corresponding projecting portions 46 and in a shape and a size into which the corresponding projecting portions 46 are capable of being fitted. It is preferable for the recessed portions 32A and 34A to be given a shape and a size with which the compression paddle 40 is stably supported when the projecting portions 46 of the compression paddle 40 have been fitted into them.

It is preferable for the two projecting portions 46 of the four projecting portions 46 that are placed on at least one diagonal line to be formed so as to have mutually different shapes or sizes in order to make it easy to distinguish the front and rear directions of the compression paddle 40.

Figure 14A:
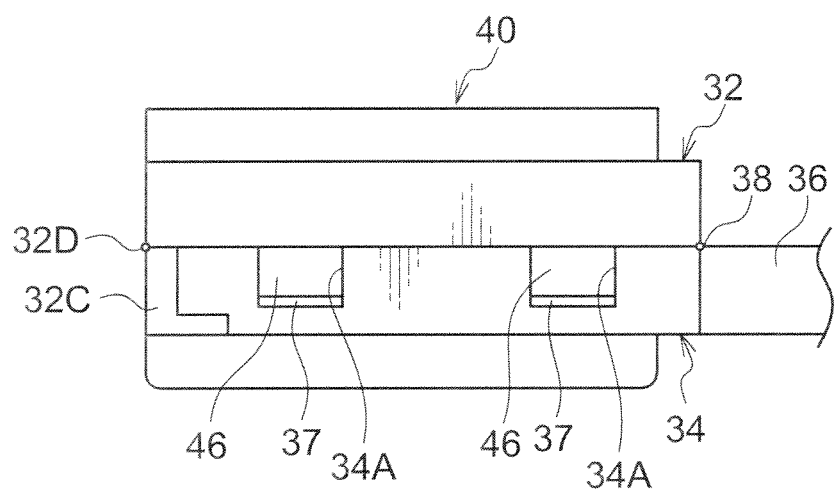
FIG. 14A and FIG. 14B are side views showing a modification of the compression paddle support portion.

In the above exemplary embodiment, the recessed portions are formed in the first divisional member 32 and in the second divisional member 34, but embodiments are not limited to this. For example, as shown in FIG. 14A, the recessed portions 34A may be formed only in the second divisional member 34 and the recessed portions 32A may not be formed in the first divisional member 32. In this case, the projecting portions 46 of the compression paddle 40 become fitted into only the recessed portions 34A of the second divisional member 34, so the recessed portions 34A may be formed such that the depth of the recessed portions 34A is a depth sufficient enough for the projecting portions 46 to be able to fit into the recessed portions 34A as far as the upper surfaces of the projecting portions 46.

Figure 14B:
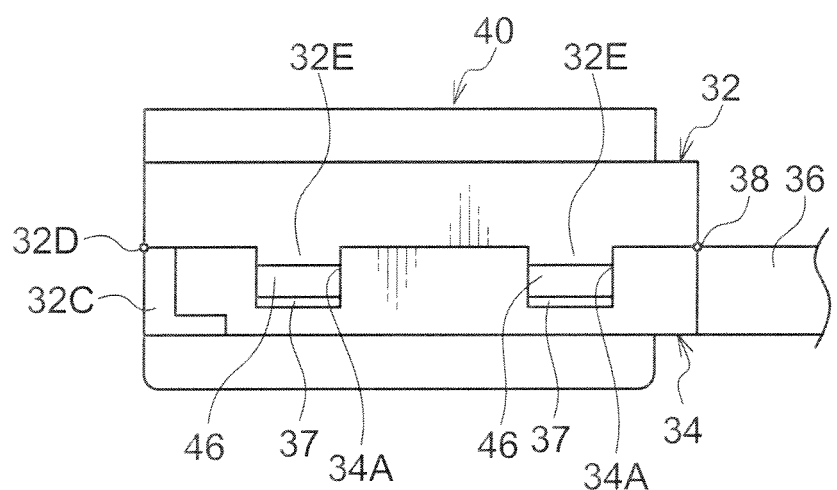

Moreover, as shown in FIG. 14B, convex portions 32E may be formed on the first divisional member 32 in positions corresponding to the projecting portions 46 of the compression paddle 40 and the recessed portions 34A may be formed in the second divisional member 34 in positions corresponding to the projecting portions 46 of the compression paddle 40. In this case, the recessed portions 34A may be formed such that the depth of the recessed portions 34A is a depth sufficient enough for the convex portions 32E of the first divisional member 32 to be able to fit into them in a state where the projecting portions 46 have been fitted into the recessed portions 34A. In FIG. 14B also, it is desirable for the corner portions of the convex portions 32E and the recessed portions 34A to be chamfered.

In the above exemplary embodiment, a the pressure sensors 37 are disposed in all of the four recessed portions 34A of the second divisional member 34, but embodiments are not limited to this. For example, the pressure sensors 37 may be disposed in two or three of the recessed portions 34A rather than in all of the recessed portions 34A.

In the above exemplary embodiment, the projecting portions 46 are disposed two each on the opposing pair of outer peripheral surfaces of the outer peripheral wall 44, but embodiments are not limited to this. For example, three or more of the projecting portions 46 may be disposed on the opposing pair of outer peripheral surfaces of the outer peripheral wall 44, or the projecting portions 46 may be disposed one each on the opposing pair of outer peripheral surfaces of the outer peripheral wall 44. In a case where the projecting portions 46 are disposed one each on the pair of outer peripheral surfaces like in the latter case, the shape of the projecting portions 46 may be given an elongate shape extending along the X direction, and the recessed portions 32A and the recessed portions 34A of the first divisional member 32 and the second divisional member 34 may be given an elongate shape matching the shape and the size of the projecting portions 46. By this configuration, the compression paddle 40 can be stably supported in the compression paddle support portion 30. The pressure sensors 37 may be disposed several each in the elongate recessed portions 34A. In this case, the recessed portions 46A of the projecting portions 46 are also multiply disposed in positions according to the pressure sensors 37.

Figure 15A:
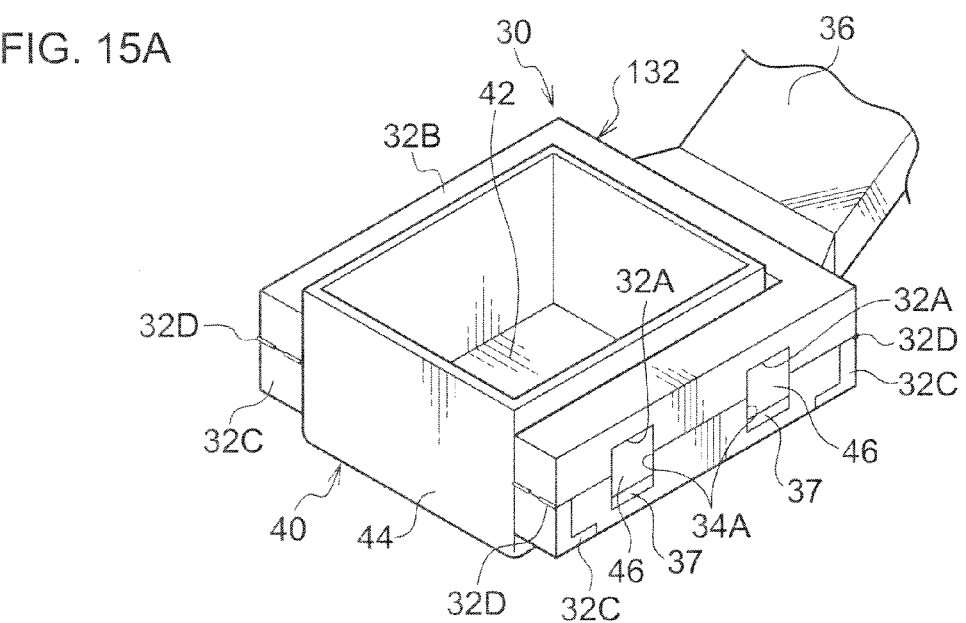
FIG. 15A and FIG. 15B are perspective views showing a modification of the compression paddle support portion.
Figure 15B:
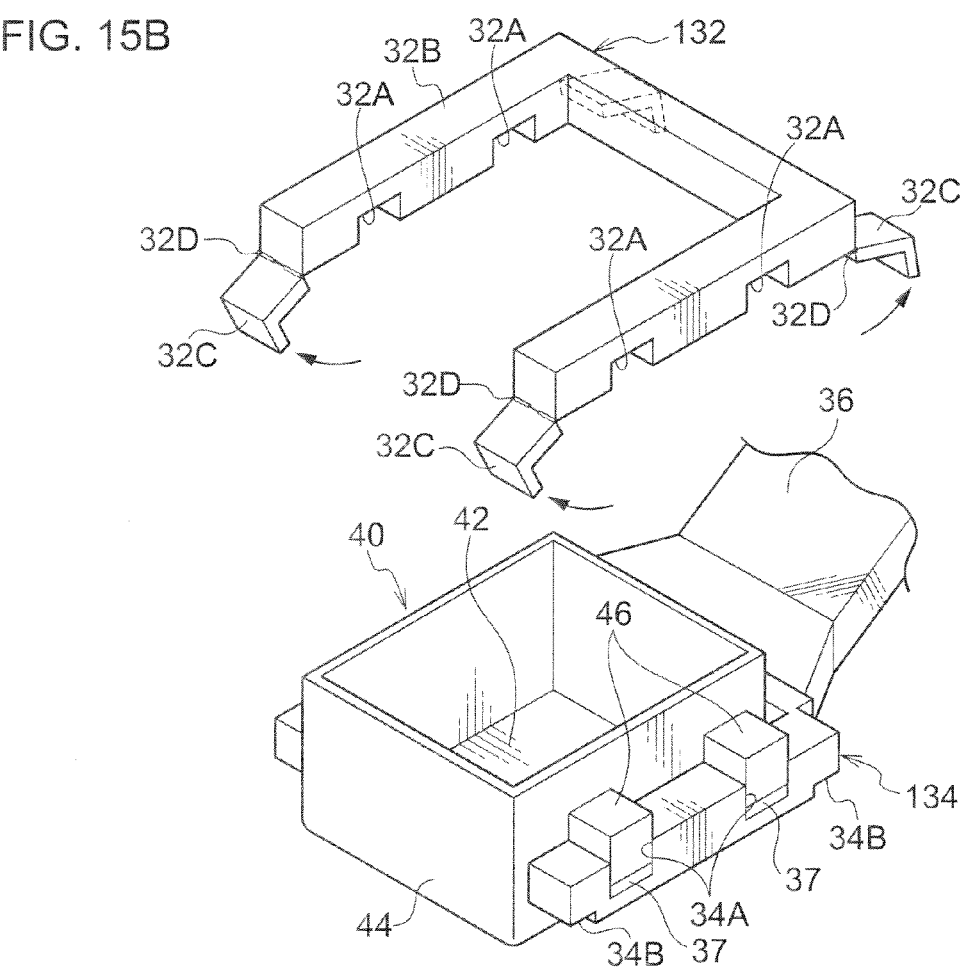

In the above exemplary embodiment, the first divisional member 32 is configured rotatable with respect to the second divisional member 34, but embodiments are not limited to this. For example, the first divisional member 32 may be configured separable (detachable) with respect to the second divisional member 34. FIG. 15A and FIG. 15B show an example of the compression paddle support portion 30 that has a first divisional member 132 and a second divisional member 134 configured separable in this way.

FIG. 15A is a perspective view showing the compression paddle support portion 30 and the compression paddle 40 when the compression paddle 40 has been attached to the compression paddle support portion 30 and the compression paddle support portion 30 has been placed in the closed state (a state where the lower surface of the first divisional member 132 and the upper surface of the second divisional member 134 are contacting each other). FIG. 15B is a perspective view showing a state where the projecting portions 46 of the compression paddle 40 have been fitted into the recessed portions 34A of the second divisional member 134 of the compression paddle support portion 30 in the open state (a state where the lower surface of the first divisional member 132 and the upper surface of the second divisional member 134 are apart from each other).

The second divisional member 134 is formed in a substantially square C shape as seen in a side view and is coupled in a fixed state to the sliding support portion 39 via the coupling portion 36. The recessed portions 34A are formed in the second divisional member 134 in positions corresponding to the projecting portions 46 disposed on the compression paddle 40. The cutout portions 34B are formed in the two distal end portions of the second divisional member 134. The cutout portions 34B are also formed in the two corner portions on the coupling portion 36 side of the second divisional member 134. The pressure sensors 37 are disposed on the bottom surfaces of the recessed portions 34A of the second divisional member 134.

The first divisional member 132 is formed in a substantially square C shape as seen in a plan view, and the multiple recessed portions 32A are formed in the body 32B thereof. The engaging portions 32C are coupled to the body 32B of the first divisional member 32 via the hinge portions 32D, and the engaging portions 32C are configured to be rotatable with respect to the body 32B. The engaging portions 32C of the first divisional member 132 are disposed not just on the two distal end portions of the body 32B but also on the two corner portions. That is, as shown in FIG. 15A, four of the engaging portions 32C are formed on the first divisional member 132 such that the four engaging portions 32C engage with the four cutout portions 34B of the second divisional member 134 in the closed state of the compression paddle support portion 30.

Here, the procedure of attaching the compression paddle 40 to the compression paddle support portion 30 shown in FIG. 15A and FIG. 15B will be described.

The engaging portions 32C of the first divisional member 132 are rotated and disengaged from the cutout portions 34B of the second divisional member 134. Then, the first divisional member 132 is separated from the second divisional member 134 to place the compression paddle support portion 30 in the open state. Then, the projecting portions 46 of the compression paddle 40 are brought into alignment with the positions of the recessed portions 34A of the second divisional member 134 and are fitted into the recessed portions 34A of the second divisional member 134 from above the second divisional member 134. Thereby, as shown in FIG. 15B, the lower-side portions of the projecting portions 46 of the compression paddle 40 become fitted into the recessed portions 34A. From this state, the lower surface of the body 32B of the first divisional member 132 is brought into contact with the upper surface of the second divisional member 134, and the upper-side portions of the projecting portions 46 of the compression paddle 40 are fitted into the recessed portions 32A of the first divisional member 132. Then, the four engaging portions 32C of the first divisional member 132 are engaged with the four cutout portions 34B of the second divisional member 134.

As a result, as shown in FIG. 15A, the compression paddle 40 is attached to the compression paddle support portion 30 in a state where the compression paddle 40 is sandwiched between the first divisional member 132 and the second divisional member 134 in an orientation where the pressing surface of the pressing portion 42 of the compression paddle 40 opposes the imaging surface 20. The imaging method is the same as described above, so description thereof is omitted. In the case of detaching the compression paddle 40 from the compression paddle support portion 30, it suffices to perform the reverse procedure of the above attachment procedure.

Figure 16A:
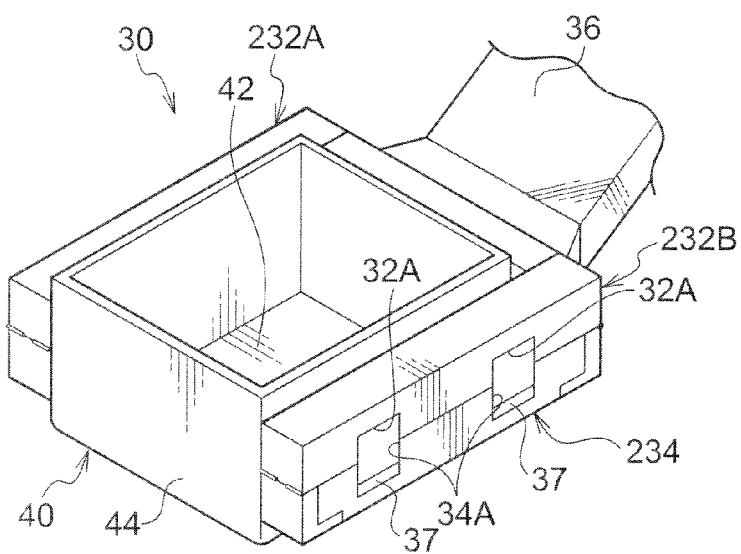
FIG. 16A and FIG. 16B are perspective views showing a modification of the compression paddle support portion.
Figure 16B:
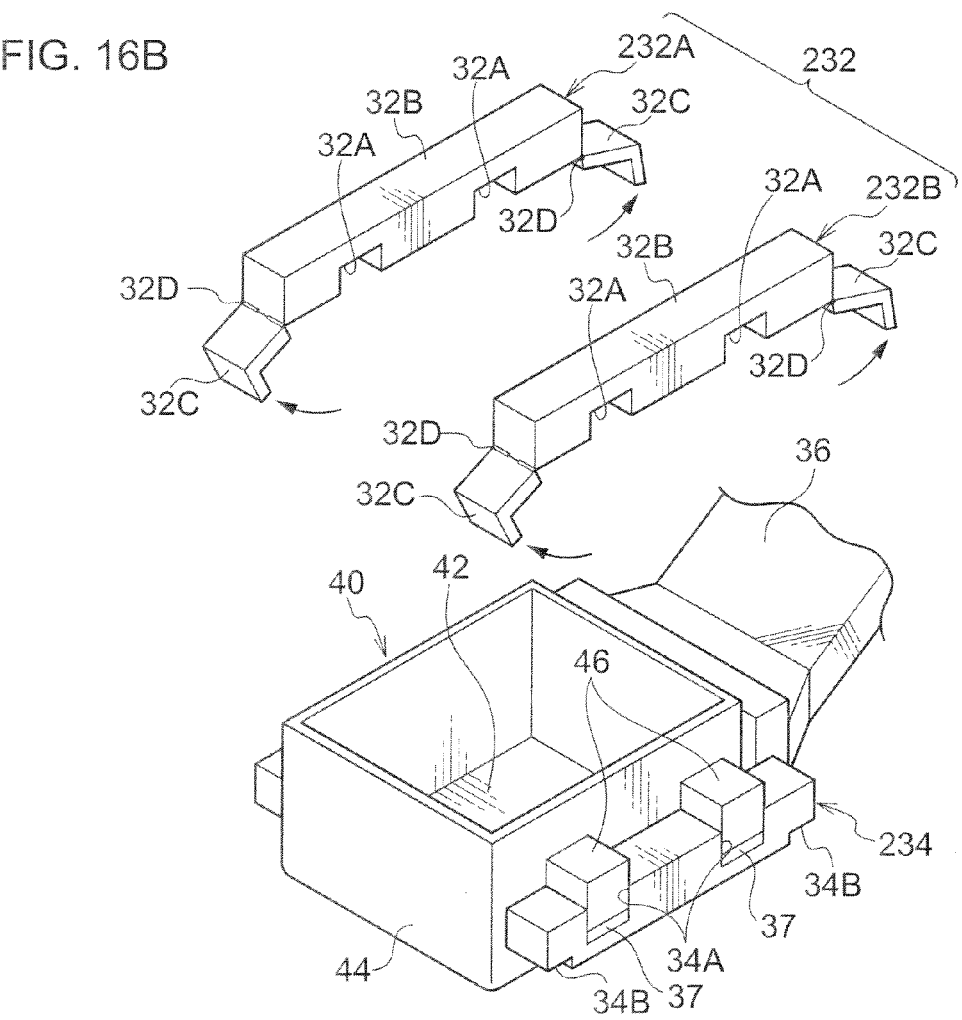

The first divisional member 132 may be configured such that it is further divided into two members. As shown in FIG. 16A and FIG. 16B, the compression paddle support portion 30 is configured to include a first divisional member 232 and a second divisional member 234 that are separable, and the first divisional member 232 is further configured by a member 232A and a member 232B that are mutually separate.

FIG. 16A is a perspective view showing the compression paddle support portion 30 and the compression paddle 40 when the compression paddle 40 has been attached to the compression paddle support portion 30 and the compression paddle support portion 30 has been placed in the closed state (a state where the lower surfaces of the member 232A and the member 232B of the first divisional member 232 and the upper surface of the second divisional member 234 are contacting each other). FIG. 16B is a perspective view showing a state where the projecting portions 46 of the compression paddle 40 have been fitted into the recessed portions 34A of the second divisional member 234 of the compression paddle support portion 30 in the open state (a state where the lower surfaces of the member 232A and the member 232B of the first divisional member 232 and the upper surface of the second divisional member 234 are apart from each other).

The members 232A and 232B configuring the first divisional member 232 are both equipped with a substantially rectangular parallelepiped body 32B, and the multiple recessed portions 32A are disposed in the bodies 32B. The engaging portions 32C are coupled via the hinge portions 32D to both ends of the bodies 32B, and the engaging portions 32C are configured rotatable with respect to the bodies 32B. Due to this configuration, the four engaging portions 32C disposed on the members 232A and 232B of the first divisional member 232 engage with the four cutout portions 34B of the second divisional member 234 when the compression paddle support portion 30 has been placed in the closed state.

The configuration of the second divisional member 234 is similar to that of the second divisional member 134 shown in FIG. 15B, so description thereof is omitted.

The procedure of attaching the compression paddle 40 to the compression paddle support portion 30 shown in FIG. 16A and FIG. 16B will be described.

As shown in FIG. 16B, the engaging portions 32C of the bodies 32B of the members 232A and 232B of the first divisional member 232 are rotated and disengaged from the cutout portions 34B of the second divisional member 234. Then, in a state where the members 232A and 232B of the first divisional member 232 have been separated from the second divisional member 234, the compression paddle support portion 30 is placed in the open state. Then, the projecting portions 46 of the compression paddle 40 are brought into alignment with the positions of the recessed portions 34A of the second divisional member 234 and are fitted into the recessed portions 34A of the second divisional member 234 from above the second divisional member 234. As a result, as shown in FIG. 16B, the lower-side portions of the projecting portions 46 of the compression paddle 40 become fitted into the recessed portions 34A. From this state, the lower surfaces of the bodies 32B of the members 232A and 232B of the first divisional member 232 are brought into contact with the upper surface of the second divisional member 234, and the upper-side portions of the projecting portions 46 of the compression paddle 40 are fitted into the recessed portions 32A of the members 232A and 232B of the first divisional member 232. Then, the four engaging portions 32C of the first divisional member 232 are engaged with the four cutout portions 34B of the second divisional member 234.

In this way, as shown in FIG. 16A, the compression paddle 40 is attached to the compression paddle support portion 30 in a state where the compression paddle 40 is sandwiched between the first divisional member 232 and the second divisional member 234 in an orientation where the pressing surface of the pressing portion 42 of the compression paddle 40 opposes the imaging surface 20. The imaging method is the same as above, so description thereof is omitted. In the case of detaching the compression paddle 40 from the compression paddle support portion 30, it suffices to perform the reverse procedure of the above attachment procedure.

In the above description, the compression paddle support portion 30 is configured such that the first divisional member and the second divisional member are adjacent in the vertical direction (the toward-and-away direction), but embodiments are not limited to this. For example, the compression paddle support portion 30 may be configured such that the first divisional member and the second divisional member are adjacent in the left-right direction (a direction intersecting the toward-and-away direction).

Figure 17:
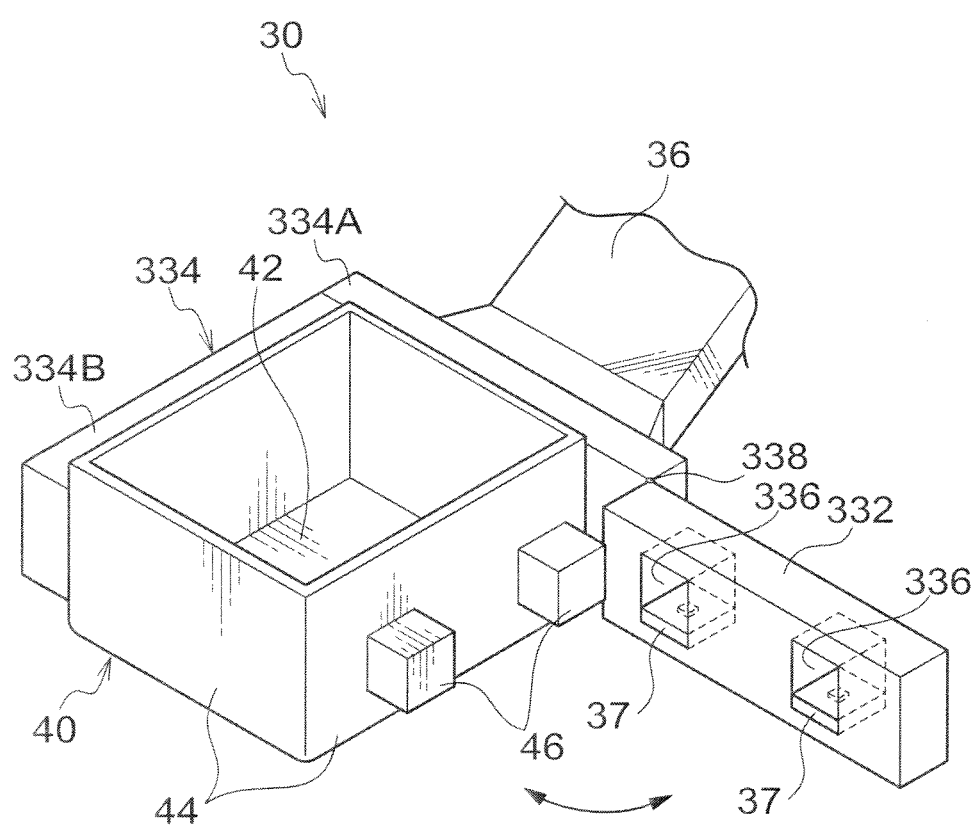
FIG. 17 is a perspective view showing a modification of the compression paddle support portion.

For example, as shown in FIG. 17, a second divisional member 334 may be formed in a substantial L shape when seen in a plan view by fixedly interconnecting one end of a member 334A, which is coupled in a fixed state to the sliding support portion 39 via the coupling portion 36, and one end of a member 334B, in which are formed multiple recessed portions 336 (not shown in FIG. 17) into which the projecting portions 46 of the compression paddle 40 fit. In the recessed portions 336 of the second divisional member 334, the pressure sensors 37 are disposed on the side surface of the four side surfaces of each of the recessed portions 336 where the pressure becomes the largest in a state where the compression paddle 40 is attached to the compression paddle support portion 30 and does not contact the breast. A first divisional member 332 is formed in a substantially rectangular parallelepiped shape. Like the member 334B of the second divisional member 334, multiple recessed portions 336 into which the projecting portions 46 of the compression paddle 40 fit are formed in the first divisional member 332. In the recessed portions 336 of the first divisional member 332, the pressure sensors 37 are disposed on the side surface of the four side surfaces of each of the recessed portions 336 where the pressure becomes the largest in a state where the compression paddle 40 is attached to the compression paddle support portion 30 and does not contact the breast.

One end of the first divisional member 332 and one end of the second divisional member 334 are coupled together via a hinge portion 338. The first divisional member 332 is configured rotatable in the direction illustrated in FIG. 17 with respect to the second divisional member 334. The compression paddle support portion 30 is configured such that, in a case where the compression paddle support portion 30 is in the closed state, the side surface of the first divisional member 332 in which the recessed portions 336 are disposed and the side surface of the member 334B of the second divisional member 334 in which the recessed portions 336 are disposed oppose each other in a state where they are apart from each other equal to or greater than the left-right direction width of the outer peripheral wall 44 of the compression paddle 40.

The procedure of attaching the compression paddle 40 to the compression paddle support portion 30 shown in FIG. 17 will be described.

First, the first divisional member 332 is rotated in the direction away from the member 334B of the second divisional member 334 to place the compression paddle support portion 30 in the open state. Then, the projecting portions 46 formed on one of the opposing pair of outer peripheral surfaces of the outer peripheral wall 44 of the compression paddle 40 are fitted into the recessed portions 336 disposed in the member 334B of the second divisional member 334. From this state (the state shown in FIG. 17), the first divisional member 332 is rotated in the direction toward the member 334B of the second divisional member 334 to place the compression paddle support portion 30 in the closed state. Thereby, the projecting portions 46 disposed on the other outer peripheral surface of the outer peripheral wall 44 of the compression paddle 40 are fitted into the recessed portions 336 of the first divisional member 332.

In this way, the compression paddle 40 is attached to the compression paddle support portion 30 in a state where the compression paddle 40 is sandwiched between the first divisional member 332 and the second divisional member 334 in an orientation where the pressing surface of the pressing portion 42 of the compression paddle 40 opposes the imaging surface 20. The imaging method is the same as above, so description thereof is omitted. In the case of detaching the compression paddle 40 from the compression paddle support portion 30, it suffices to perform the reverse procedure of the above attachment procedure.

It is preferable for the corner portions of the projecting portions 46 and the recessed portions 336 to be formed in a chamfered state so that the projecting portions 46 of the compression paddle 40 easily fit into the recessed portions 336 of the first divisional member 332, but illustration thereof is omitted in FIG. 17 used in the above description. Likewise, chamfering may also be administered to the protruding portions 37A of the pressure sensors 37 so that the projecting portions 46 easily fit into the recessed portions 336.

Here, an example where the multiple recessed portions 336 were formed in one side surface of the first divisional member 332 and in one side surface of the second divisional member 334 has been described, but embodiments are not limited to this. For example, instead of the recessed portions 336, hole portions penetratingly formed from one side surface to the other side surface may be formed in the first divisional member 332 and the second divisional member 334 as the fitting portions into which the projecting portions 46 of the compression paddle 40 are fitted.

Figure 18A:
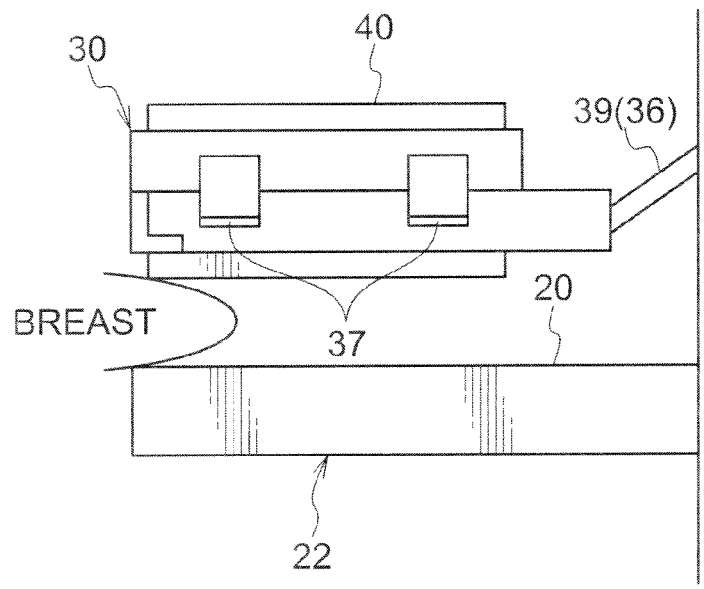
FIG. 18A is a schematic configuration diagram of an example in which an imaging table doubles as a subject table.
Figure 18B:
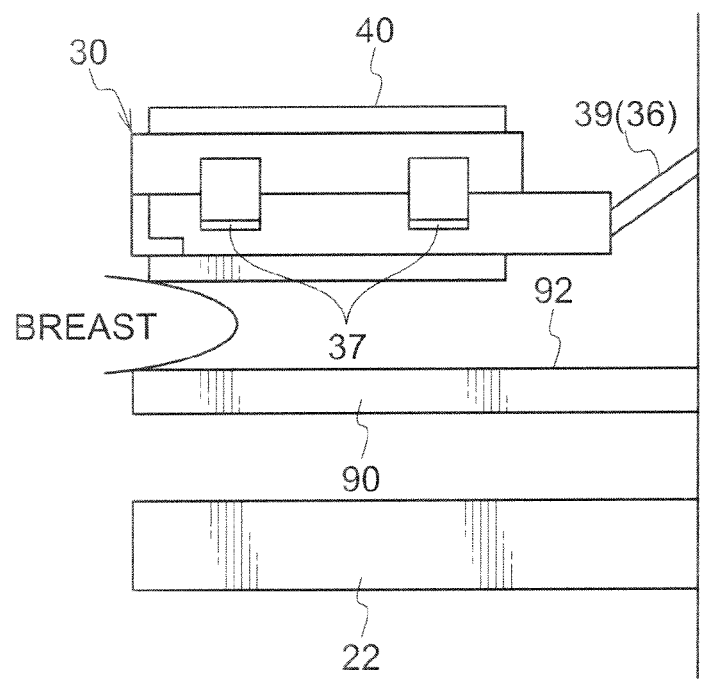
FIG. 18B is a schematic configuration diagram of an example in which an imaging table and a subject table are disposed independent of one another.

In the above exemplary embodiment and its modifications, as shown in FIG. 18A, the imaging table 22 that has the radiation detector (not shown) is disposed and the compression paddle 40 presses the breast of the subject against the imaging surface 20 of the imaging table 22, but embodiments are not limited to this. For example, as shown in FIG. 18B, a subject table 90 on which a breast that is an imaging subject is placed may be provided separate from the imaging table 22, the compression paddle 40 may press the breast against a pressed surface 92 of the subject table 90, and the imaging surface 20 disposed under the subject table 90 may capture a subject image. The subject table 90 is configured by a material that allows radiation to pass therethrough.

In the above exemplary embodiment and its modifications, the compression paddle support portion 30 is configured to be movable in the toward-and-away direction toward and away from the imaging surface 20 of the imaging table 22, but embodiments are not limited to this. For example, the imaging surface 20 may be configured to be movable in the toward-and-away direction toward and away from the compression paddle support portion 30 (in other words, toward and away from the compression paddle 40 attached to the compression paddle support portion 30) in a state where the compression paddle support portion 30 is fixed. Alternately, both the compression paddle support portion 30 and the imaging surface 20 may be configured to be movable in the toward-and-away direction.

Moreover, in a case where the subject table 90 is provided apart from the imaging table 22 as shown in FIG. 18B, the subject table 90 may be configured to be movable in the toward-and-away direction toward and away from the compression paddle support portion 30 (in other words, toward and away from the compression paddle 40 attached to the compression paddle support portion 30). Conversely, the compression paddle support portion 30 may be configured to be movable in the toward-and-away direction toward and away from the subject table 90. Alternately, both the compression paddle support portion 30 and the subject table 90 may be configured to be movable.

Figure 19A:
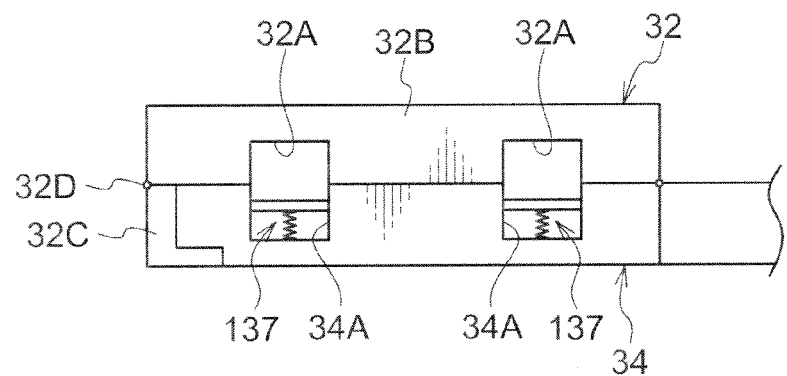
FIG. 19A to FIG. 19C are side views showing a modification of the pressure sensors.
Figure 19B:
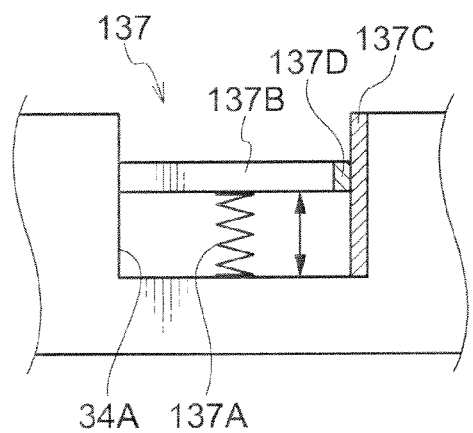
Figure 19C:
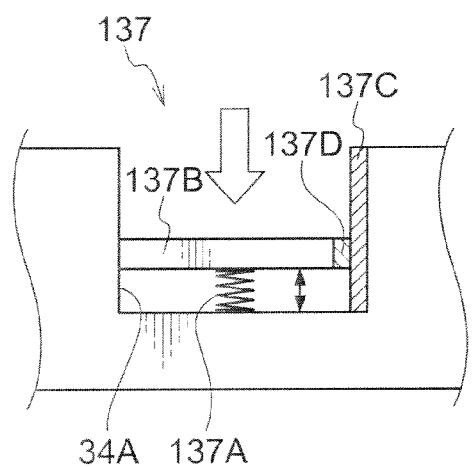

The pressure sensors disposed in the compression paddle support portion 30 are not limited to the pressure sensors 37 that detect pressure with a strain gauge as exemplified above. For example, the pressure sensors may also be pressure sensors that measure pressure by replacing it with a physical value representing length and estimate pressure from the physical value representing length to thereby indirectly detect the pressure. FIG. 19A to FIG. 19C show an example of pressure sensors 137 that detect pressure without using a strain gauge.

As shown in FIG. 19A to FIG. 19C, each of the pressure sensors 137 is equipped with a spring 137A that has one end connected to the bottom surface of the recessed portion 34A, a planar member 137B to which the other end of the spring 137A is connected and which contacts the compression paddle 40, a magnetic scale 137C that is disposed on one side surface of the recessed portion 34A and to which a magnetic memory has been given, and a magnetic head 137D that is coupled to the member 137B.

When the projecting portion 46 is fitted into the recessed portion 34A, the projecting portion 46 pushes the member 137B down and the magnetic head 137D coupled to the member 137B moves. Further, the member 137B moves in response to the compression force with which the compression paddle 40 presses the breast against the imaging surface 20 (or the pressed surface 92), and the magnetic head 137D moves (see FIG. 19B and FIG. 19C). When the magnetic head 137D moves along the magnetic scale 137C, it outputs an electrical signal. The displacement of the magnetic head 137D is detected from that electrical signal and the length of the spring 137A is measured. Then, the pressure is calculated by a predetermined function representing the relationship between the length of the spring 137A and pressure. Alternately, a table in which lengths of the spring 137A and pressures are corresponded with one another may be stored beforehand, and the pressure may be determined from that table.

Here, pressure sensors that measure the lengths of the springs 137A by magnetism and detect pressure have been taken as an example and described, but embodiments are not limited to this. For example, the pressure sensors may also be pressure sensors that measure the lengths of the springs 137A by a change in electrical resistance and detect pressure, or the pressure sensors may be configured such that, by irradiating laser light, they measure the positions of the members 137B and detect pressure.

In the above exemplary embodiment and its modifications, the pressure sensors 37 and 137 are disposed on the surface where the pressure drops as the compression paddle 40 presses the breast against the imaging surface 20 (or the pressed surface 92) has been described, but embodiments are not limited to this. For example, the pressure sensors 37 and 137 may be disposed on the surface where the pressure increases as the compression paddle 40 presses the breast against the imaging surface 20 (or the pressed surface 92). Further, the pressure sensors 37 and 137 may be disposed on both the surface where the pressure increases and the surface where the pressure drops.

In the above exemplary embodiment and its modifications, the compression paddle support portion 30 in which the first divisional member is coupled so as to be rotatable with respect to the second divisional member, or the compression paddle support portion 30 in which the first divisional member is configured so as to be separable with respect to the second divisional member, but embodiments are not limited to this. The first divisional member may be coupled in a fixed state to the slide holding member 39, with the second divisional member being coupled and configured rotatable (or configured separable) with respect to the first divisional member.

In a case where a bias equal to or greater than a predetermined bias has been detected in the pressure distribution determined by the arithmetic circuit 74, the arithmetic circuit 74 may generate a control signal with respect to the power unit control circuit 76 so that the compression action stops, output the control signal to the power unit control circuit 76, and stop the moving of the sliding support portion 39. Further, a warning may be displayed on the display 100. Thereby, unnecessary pain can be prevented from being imparted to the subject in a case where the technologist has compressed the breast of the subject in a biased pressure distribution.

The present invention is not limited to the embodiment described above, and various design changes can be made in the scope of the invention described in the claims.

The invention claimed is:

1. A radiographic image capturing device comprising:
   a subject table that comprises a pressed surface against which a breast of a subject is pressed; and
   a compression paddle support portion that comprises a first member and a second member, and to which a compression paddle is attached by sandwiching the compression paddle between the first member and the second member, and comprises multiple pressure sensors for detecting pressures applied to multiple sites of the attached compression paddle,
   wherein at least one of the subject table or the compression paddle support portion is movable in a first direction that is toward and away from one another.

2. The radiographic image capturing device according to claim 1, further comprising the compression paddle that is detachable and comprises a pressing portion that presses the breast against the pressed surface.

3. The radiographic image capturing device according to claim 1, wherein the multiple pressure sensors are disposed in at least one of the first member or the second member.

4. The radiographic image capturing device according to claim 1, wherein the multiple pressure sensors are disposed on surfaces that contact the compression paddle in a state where the compression paddle has been attached.

5. The radiographic image capturing device according to claim 1, wherein the multiple pressure sensors are disposed on surfaces where pressure drops or increases as the compression paddle presses the breast against the pressed surface.

6. The radiographic image capturing device according to claim 1, wherein one of the first member or the second member is coupled so as to be rotatable with respect to the other.

7. The radiographic image capturing device according to claim 1, wherein one of the first member or the second member is disposed so as to be separable with respect to the other.

8. The radiographic image capturing device according to claim 1, wherein the compression paddle support portion is configured such that the first member and the second member are adjacent in the first direction or in a second direction intersecting the first direction.

9. The radiographic image capturing device according to claim 1, wherein
   the compression paddle comprises a pressing portion that presses the breast against the pressed surface, an outer peripheral wall that is disposed upright along an outer peripheral edge of the pressing portion, and multiple projecting portions that are formed on outer peripheral surfaces of the outer peripheral wall,
   at least one of the first member or the second member comprises multiple fitting portions corresponding to the multiple projecting portions of the compression paddle,
   the pressure sensors are disposed in two or more fitting portions of the multiple fitting portions, and
   the compression paddle is attached by sandwiching the projecting portions between the first member and the second member in a state where the projecting portions have been fitted into the fitting portions.

10. The radiographic image capturing device according to claim 9, wherein
   each of the multiple pressure sensors comprises a protruding portion that contacts and is pressurized by corresponding projecting portion, the multiple pressure sensors detecting pressures applied to the protruding portions, and each of the projecting portions comprises a recessed portion shallower than the protruding height of the protruding portions in a position corresponding to the protruding portion of the pressure sensor in a state where the projecting portions have been fitted into the fitting portions.

11. A detachable compression paddle comprising:
a pressing portion that presses a breast against the pressed surface of the radiographic image capturing device according to claim 9;
an outer peripheral wall that is disposed upright along an outer peripheral edge of the pressing portion; and
multiple projecting portions that are formed on outer peripheral surfaces of the outer peripheral wall portion in correspondence to the fitting portions of the compression paddle support portion,
wherein the compression paddle is attached to the compression paddle support portion as a result of the projecting portions being sandwiched between the first member and the second member in a state where the projecting portions have been fitted into the fitting portions of the compression paddle support portion.

12. A radiographic image capturing device comprising:
a subject table that comprise's a pressed surface against which a breast of a subject is pressed;
a detachable compression paddle that comprises a pressing portion that presses the breast against the pressed surface; and
a compression paddle support portion that comprises a first member and a second member, and to which the compression paddle is attached by sandwiching the compression paddle between the first member and the second member, and comprises multiple pressure sensors for detecting pressures applied to multiple sites of the attached compression paddle,
wherein at least one of the subject table or the compression paddle support portion is movable in a first direction that is toward and away from one another.

\* \* \* \* \*